United States Patent
Cole et al.

(10) Patent No.: US 9,421,030 B2
(45) Date of Patent: Aug. 23, 2016

(54) FOLLICULAR DISSECTION DEVICE AND METHOD

(75) Inventors: John P. Cole, Alpharetta, GA (US); Tesfaye H. Gutema, Alpharetta, GA (US); Howard L. Paulk, Cumming, GA (US)

(73) Assignee: Cole Isolation Technique, LLC, Alpharetta, GA (US)

( * ) Notice: Subject to any disclaimer, the term of this patent is extended or adjusted under 35 U.S.C. 154(b) by 503 days.

(21) Appl. No.: 12/618,588

(22) Filed: Nov. 13, 2009

(65) Prior Publication Data
US 2010/0125287 A1 May 20, 2010

Related U.S. Application Data

(60) Provisional application No. 61/114,947, filed on Nov. 14, 2008.

(51) Int. Cl.
| | |
|---|---|
| *A61B 17/3205* | (2006.01) |
| *A61B 17/322* | (2006.01) |
| *A61B 17/00* | (2006.01) |
| *A61B 17/32* | (2006.01) |

(52) U.S. Cl.
CPC ......... *A61B 17/32053* (2013.01); *A61B 17/322* (2013.01); *A61B 17/32002* (2013.01); *A61B 2017/00137* (2013.01); *A61B 2017/00398* (2013.01); *A61B 2017/00752* (2013.01)

(58) Field of Classification Search
CPC ........... A61B 17/32053; A61B 17/322; A61B 2017/00752; A61B 2017/00398; A61B 2017/00137; A61B 17/32002; A45D 26/0023; A45D 26/0042

USPC ......... 606/167, 185, 159, 180, 133, 170, 171, 606/184, 187; 600/562–572; 318/255–259
See application file for complete search history.

(56) References Cited

U.S. PATENT DOCUMENTS

| | | | | |
|---|---|---|---|---|
| 5,782,843 | A * | 7/1998 | Aasberg | 606/133 |
| 7,172,604 | B2 * | 2/2007 | Cole | 606/131 |
| 8,690,894 | B2 * | 4/2014 | Bodduluri | A61B 17/32053 606/133 |
| 2003/0004526 | A1 * | 1/2003 | Austring et al. | 606/166 |
| 2003/0040766 | A1 * | 2/2003 | Werner | 606/187 |
| 2003/0097144 | A1 | 5/2003 | Lee | |
| 2006/0178678 | A1 * | 8/2006 | Cole | 606/133 |
| 2007/0078475 | A1 * | 4/2007 | Bodduluri et al. | 606/187 |
| 2007/0156164 | A1 * | 7/2007 | Cole et al. | 606/187 |
| 2007/0255293 | A1 * | 11/2007 | Corre | 606/133 |
| 2008/0234602 | A1 * | 9/2008 | Oostman et al. | 600/564 |

FOREIGN PATENT DOCUMENTS

| | | |
|---|---|---|
| KR | 10-0512694 | 9/2005 |
| KR | 10-2007-0037577 | 4/2007 |

(Continued)

OTHER PUBLICATIONS dictionary.com definition of "driver" accessed Dec. 19, 2014.*

(Continued)

*Primary Examiner* — Ryan J Severson
*Assistant Examiner* — Rachel S Papeika
(74) *Attorney, Agent, or Firm* — Berkeley Law & Technology Group LLP

(57) ABSTRACT

Subject matter disclosed herein relates to surgical instruments and methods for extracting hair follicles.

36 Claims, 10 Drawing Sheets

(56) References Cited

FOREIGN PATENT DOCUMENTS

| WO | 2007-041267 | 4/2007 |
| WO | 2007-293884 | 12/2007 |

OTHER PUBLICATIONS

PCT/US2009/064424/ 030.P007PCT: PCT application as filed on Nov. 13, 2009, 64 pages.

PCT/US2009/064424/ 030.P007PCT: Initial Publication without International Search Report on May 20, 2010, 64 pages.

PCT/US2009/064424/ 030.P007PCT: International Search Report mailed Jun. 14, 2010, 3 pages.

PCT/US2009/064424/ 030.P007PCT: Written Opinion of the International Search Authority, mailed Jun. 14, 2010, 5 pages.

PCT/US2009/064424/ 030.P007PCT: International Preliminary Report on Patentability mailed May 17, 2011, 6 pages.

* cited by examiner

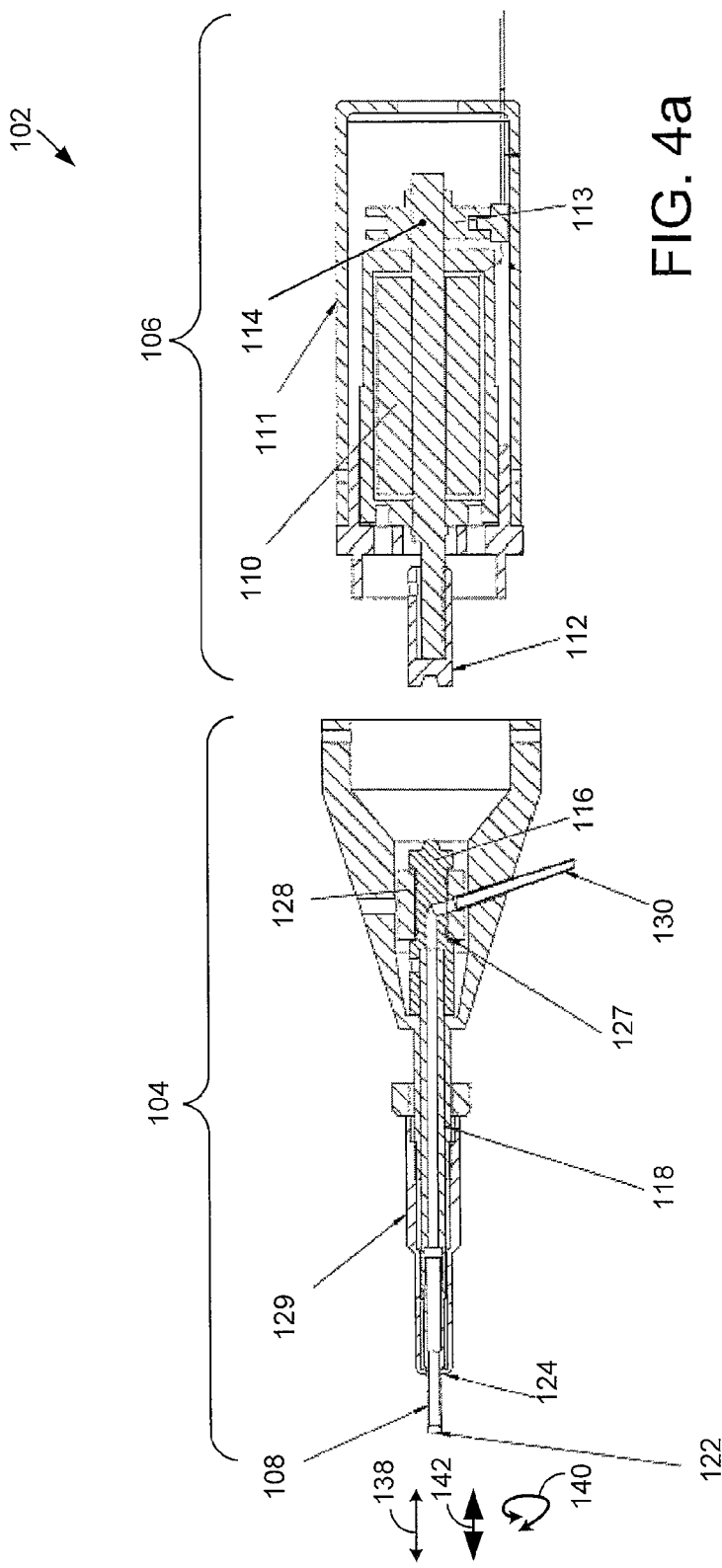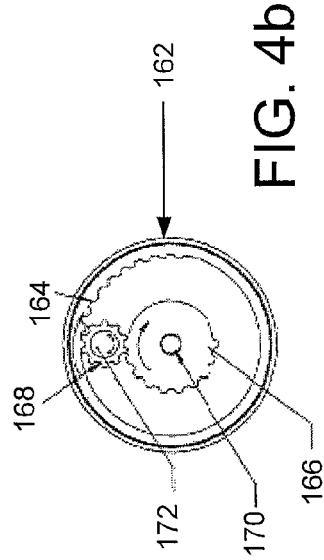
FIG. 4a
FIG. 4b

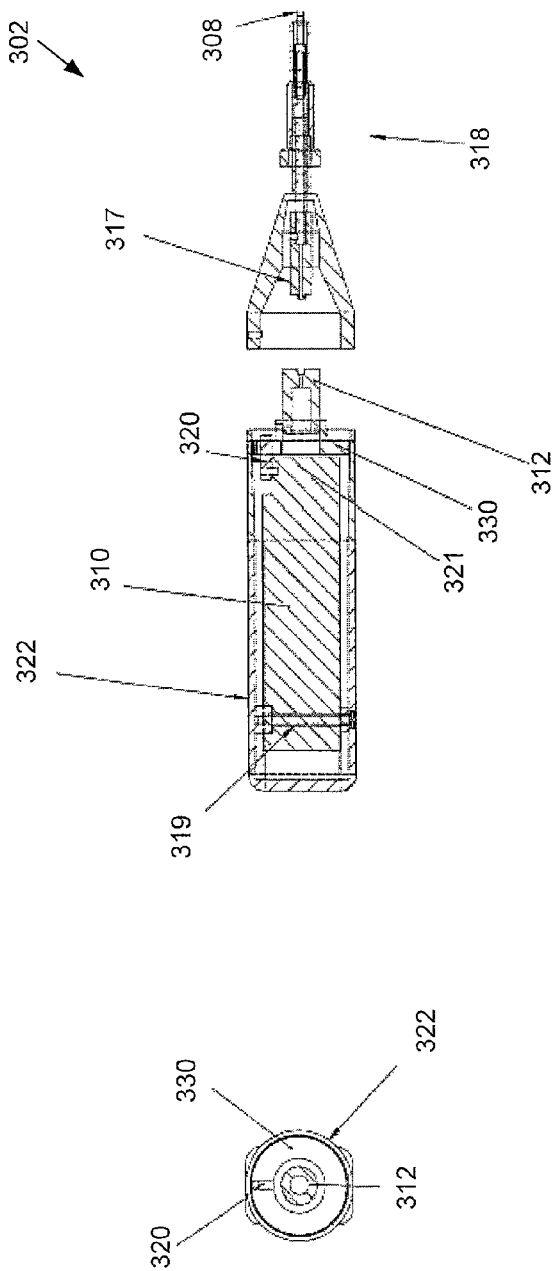
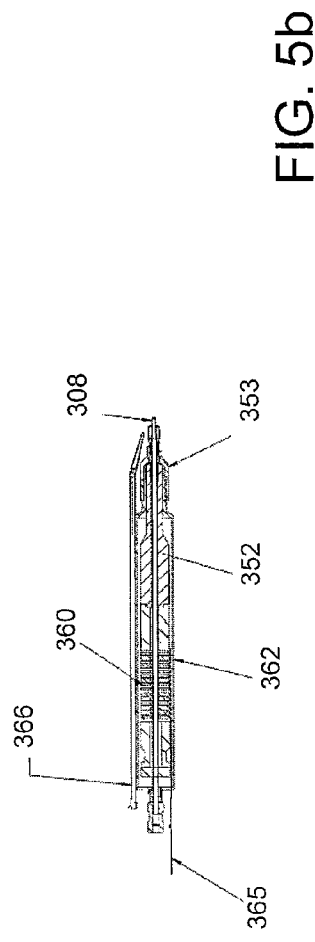
FIG. 5a
FIG. 5b ns in detail so as not to obscure claimed subject matter.

FOLLICULAR DISSECTION DEVICE AND METHOD

PRIORITY TO RELATED APPLICATIONS

This application claims priority to U.S. Provisional Application No. 61/114,947, filed Nov. 14, 2008 by John P. Cole and Tesfaye H. Gutema, entitled "Programmable Follicular Dissection Assembly and Method."

FIELD

This disclosure relates to surgical instruments and methods for extracting hair follicles.

BACKGROUND

In hair transplantation procedures, hair may be extracted from the scalp of a subject in one area of the scalp, referred to as a "donor" region, and may then be implanted in another area, referred to as a "recipient" region. These procedures may be time-consuming and require considerable specialized expertise because of the minute dimensions of individual hair follicles, the large number of individual follicles involved in a given transplantation, variability in the size or depth of hair follicles, hair angle, the fragility of hair follicles, and the variation in dermal characteristics upon which the procedure is performed.

DESCRIPTION OF THE DRAWING FIGURES

Claimed subject matter is particularly pointed out and distinctly claimed in the concluding portion of the specification. However, both as to organization and/or method of operation, together with objects, features, and/or advantages thereof, it may best be understood by reference to the following detailed description when read with the accompanying drawings in which:

FIGS. 4a through 10 are schematic diagrams of exemplary follicular dissection devices, in accordance with various embodiments.

Figure 1:
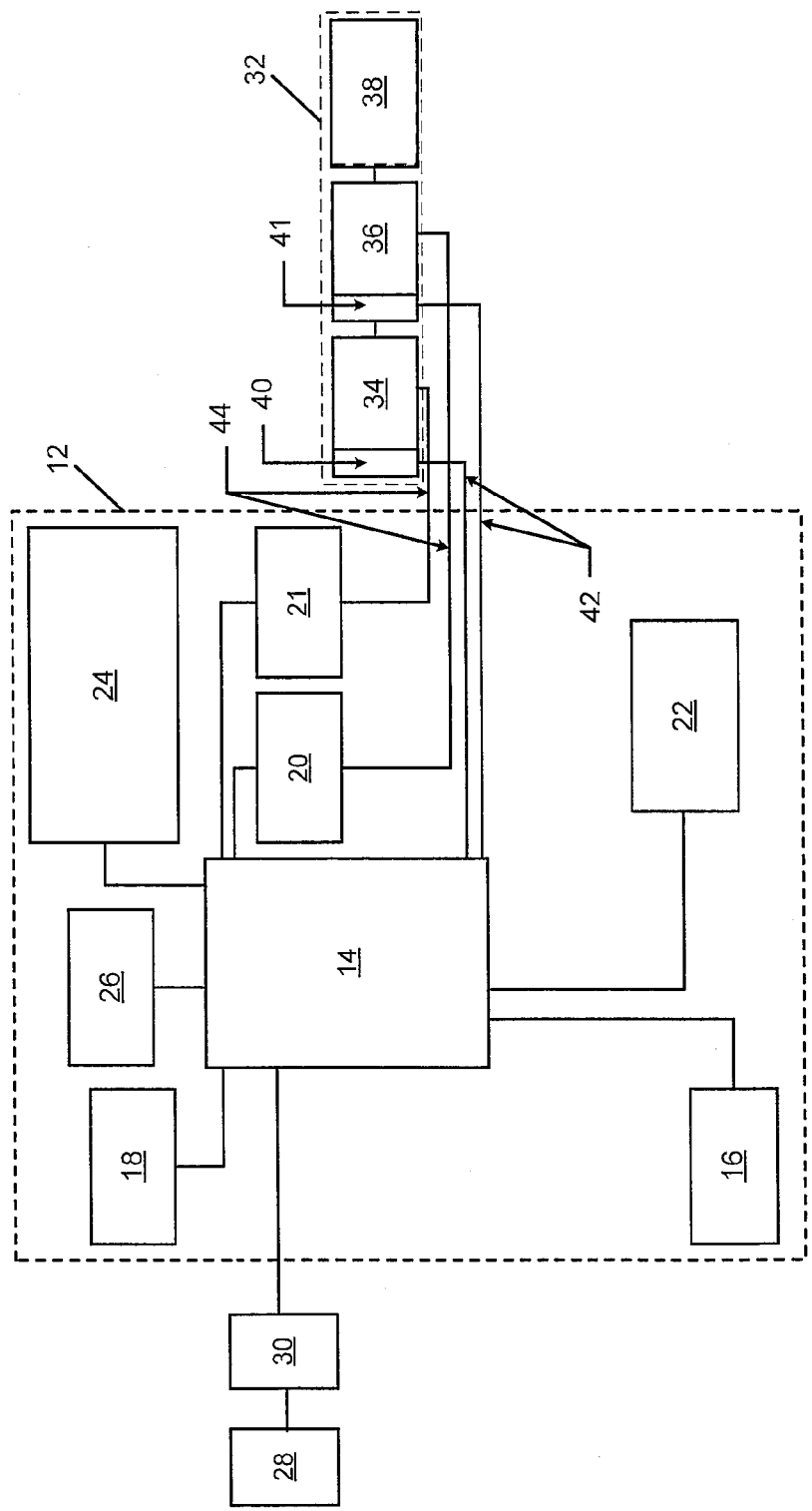
FIG. 1 is a block diagram illustrating an exemplary follicular dissection device communicatively coupled to an exemplary controller, in accordance with an embodiment.

Reference is made in the following detailed description to the accompanying drawings, which form a part of this patent application, wherein like numerals may designate like parts throughout to indicate corresponding or analogous elements. It will be appreciated that for simplicity or clarity of illustration, elements illustrated in the figures have not necessarily been drawn to scale. Further, it is to be understood that other embodiments in addition to those disclosed herein may be utilized and structural or logical changes may be made without departing from the scope of claimed subject matter. Therefore, the scope of claimed subject matter is defined by the appended claims and their equivalents; however, the following detailed description is not to be taken in a limiting sense with respect to such claimed subject matter.

DETAILED DESCRIPTION

In the following detailed description, numerous specific details are set forth to provide a thorough understanding of claimed subject matter. However, it will be understood by those skilled in the art that claimed subject matter may be practiced without these specific details. In other instances, methods, apparatuses or systems that would be known by one of ordinary skill have not been described in detail so as not to obscure claimed subject matter.

As will be described in greater detail below, methods and apparatuses may be implemented to drive a follicular extraction punch of a follicular dissection device to perform follicular dissection or extraction. FIG. 4, for example, is a schematic diagram of an exemplary follicular dissection device in accordance with an embodiment. In this exemplary embodiment, follicular dissection device 102 is depicted in a detached or decoupled position. In one example, follicular dissection device 102 may comprise a drive assembly 106 and a driven assembly 104, where driven assembly 104 may further comprise follicular extraction punch 108. In certain embodiments, coupling driven assembly 104 with drive assembly 106 may allow follicular extraction punch 108 to be moved by drive assembly 106. Here, it is noted that there may be numerous components and/or configurations for follicular dissection device 102, only some of which are described herein. Thus, the scope of claimed subject matter is not to be limited by these particular examples or illustrations.

In certain embodiments, one or more drivers of a follicular dissection device may drive a follicular extraction punch, such as punch 108, in one or more "simple motions" or "compound motions" to perform follicular dissection or extraction. In this context, the term "simple motion" refers to one or more movements of a follicular extraction punch about an axis to produce a cutting motion. For instance, in certain embodiments, one or more cutting motions associated with follicular dissection or extraction may comprise one or more rotary or oscillating cutting motions 140 about punch 108, such as may result in punch 108 to rotate in one direction (e.g., rotate), oscillate in multiple directions (e.g., rotate back and forth), and/or the like, as non-limiting examples. Also, in certain embodiments, one or more cutting motions associated with follicular extraction may comprise one or more axial motions, such as axial cutting motion 138, of a follicular extraction punch, such as may result in a punch reciprocating, vibrating, and/or the like, in an axial direction, as non-limiting example. In certain embodiments, movements of a punch in an axial direction may produce a force substantially perpendicular to a scalp if a punch were positioned substantially perpendicular to the scalp, as a non-limiting example. Of course, in certain embodiments, one or more simple motions, such as one or more of the cutting motions described above, may be produced by an operator manually rotating or oscillating a punch by manipulating a follicular dissection device, as just an example.

As mentioned above, in certain embodiments, one or more powered drivers of a follicular dissection device may drive a follicular extraction punch, such as punch 108, in one or more "compound motions" to perform follicular dissection or extraction. In this context, the term "compound motion" refers to a combination of movements of a follicular extraction punch about one or more axis to produce at least one cutting motion and at least one punch advance motion, wherein the at least one punch advance motion is applied to the punch by one or more powered drives of a follicular dissection device. Accordingly, a compound motion excludes punch advance motions generated or created solely by an operator's manual force since such motions are not generated nor created by one or more powered drives of a follicular dissection device. Accordingly, use of powered drives to apply a compound motion to a follicular dissection device may reduce operator fatigue in performing repetitive procedures, as just an example. In certain embodiments, one or more punch advance motions, such as punch advance motion 142, may comprise one or more axial extension and/or retraction motions which are operable to advance, extend and/or force a follicular extraction punch, such as punch 108, into the skin to a depth for follicular dissection and/or extraction.

To illustrate, in certain embodiments, a compound motion may comprise one or more axial cutting motions in combination with one or more axial punch advance motions, as just an example. Here, for example, one or more axial cutting motions may be superimposed over one or more axial cutting motions. To illustrate, in certain embodiments, a cutting motion may comprise axial cutting motion 138, which may move a punch a particular distance, say a particular distance ranging from 0 to 1.0 mm as just an example, back and forth from a particular starting or reference point (e.g., reciprocating or vibrating punch motion). Here, one or more punch advance motions, such as punch advance motion 142, may be superimposed over an axial cutting motion to advance and/or force a punch into the skin to a depth for follicular dissection and/or extraction. For example, during such an advance, a punch advance motion, such as punch advance motion 142, may advance a punch into the skin 1.0 mm, and then may move back to a reference position, such that stress that may be induced in the tissue may be lessened, for example. Next, a punch advance motion, such as punch advance motion 142, may move deeper into the skin, such as a depth of 2.0 mm, and then may move back to a reference position, and again may move deeper into the skin, such as a depth of 4.0 mm and then move back to a reference position, as just an example. Such punch advance motions, such as punch advance motion 142, may occur in combination with one or more axial cutting motions, such as axial motion 138, as just an example. Of course, the above illustrates merely one example of an exemplary compound motion according to an embodiment and, accordingly, the scope of claimed subject matter is not limited to this example. As just another example, in certain embodiments, a compound motion may comprise one or more rotary or oscillating cutting motions, such as rotary or oscillating cutting motions 140, in combination with one or more axial punch advance motions, such as axial punch advance motion 142.

In certain embodiments, a follicular dissection device capable of performing follicular dissection and/or extraction with a compound motion may have several advantages. For instance, in a particular embodiment, a follicular dissection device capable of performing compound motion may perform both a cutting motion and a punch advance motion. Thus, in an environment where advancing a punch may be performed by an operator manually on various devices, the capability of a drive associated with a follicular dissection device creating a punch advance motion may increase the effectiveness and precision of a particular graft and/or lessen operator fatigue from manually advancing a punch. In yet another embodiment, an advantage of a follicular dissection device capable of performing follicular dissection and/or extraction with a compound motion may be that such a device allows a particular follicular dissection and/or extraction procedure to be performed more quickly and consistently, as yet another example.

FIG. 1 is a block diagram illustrating an exemplary follicular dissection device, such as follicular dissection device 102 depicted in FIG. 4a, communicatively coupled to an exemplary controller in accordance with an embodiment. As depicted in FIG. 1, in certain embodiments, one or more drivers of follicular dissection device 32, such as drivers 34 and/or 36, may be communicatively coupled to a controller, which may produce and/or transmit signals, such as control signals 44, to one or more drivers to control movements of a follicular extraction punch. Examples of such control signals are explained in more detail below.

First, however, it is noted that a controller, such as controller 12, may comprise any device or component, or combination of devices or components, capable of transmitting signals, such as control signals 44, to one or more components associated with a follicular dissection device. In this embodiment, controller 12 may comprise various components or devices to process, store, read, display, power and/or transmit one or more signals, such as control signals 44, to a follicular dissection device. Thus, as some non-limiting examples, a controller may comprise one or more computing platforms, a microprocessor, a microcontroller, and/or like. For instance, controller 12 may include a processor 14 and memory 16, as just some examples. Here, processor 14 may comprise a central processing unit such as a microprocessor or microcontroller for executing programs, performing data manipulations, and controlling one or more tasks of controller 12. Of course, controller 12 may include a power supply 18, which may be designed to be battery powered and/or wall powered, as just some examples. In certain embodiments, power supply 18 may apply power to one or more components of controller 12, to one or more components of follicular dissection device 32, and/or other components or devices, for example.

Depending on a particular embodiment, there may be a variety of ways to couple follicular dissection device 32 with controller 12. As just some examples, follicular dissection device 32 may be connected to controller 12 via a cable, radio, and/or infrared communication, as non-limiting examples, to enable communication and/or the transmission of one or more control signals 44, one or more feedback signals 42 (feedback signals are explained below), electrical power, and/or for various other reasons. For example, a cable may be used to supply power and/or control signals from controller 12 to one or more components of follicular dissection device 32. Additionally or alternatively, radio or infrared communication (not shown) may be used to supply signals, such as control signals 44 to control one or more drivers, from controller 12 to follicular dissection device 32. For example, in certain embodiments, in order for follicular dissection device 32 to be light weight and cable free, cable connections between controller 12 and follicular dissection device 32 may be replaced by a remote control using radio frequency or infrared frequency signal, or the like. In order for follicular dissection device 32 to communicate with controller 12 via remote controls, a transmitter and a receiver (not shown) may be installed on controller 12 and follicular dissection device 32, as just an example. In addition, in certain embodiments, one or more functions of a controller, such as providing a control signal to one or more drives of a follicular dissection device, may be performed by appropriate hardware and/or software housed or disposed in a follicular dissection device. As just an example, in an embodiment, a follicular dissection device may comprise a microprocessor, memory, and/or other hardware or software allowing it to perform one or more functions of a controller.

In certain embodiments, controller 12 may include one or more user input devices, such as control switches 22, or the like. In certain embodiments, control switches 22 may be operable by hand, foot, and/or in other ways, and may comprise any number of switch types, and/or other input devices. Here, it is noted that, for simplicity, control switches 22 are shown as a single block, possibly implying that they may be a single switch or multiple switches in the same location.

While this may be the case in certain embodiments, other embodiments may have single or multiple switches in a variety of locations, such as on a follicular dissection device, on the floor as one or more footswitches and/or in other locations, which may provide one or more functions herein associated with control switches 22. Control switches 22 may enable and/or allow a user to perform various functions, specify and/or adjust various settings, and/or the like. For instance, in certain embodiments, control switches 22 may initiate a start/stop command, such as to provide a signal to start and/or stop a cycle of operation of follicular dissection device 32, based at least in part on user input. As a non-limiting example, such a stop/start cycle may comprise a single cycle of operation. In certain embodiments, control switch 22 may allow continuous operation of follicular dissection device 32 as long as a switch is depressed or kept in the "on" position, as yet another example. For instance, in certain embodiments, an operator may depress a foot pedal switch to start operation of a follicular dissection device; a follicular dissection device may cease operation if a foot pedal is released, as just an example. As yet another example, an operator may actuate a switch on a follicular dissection device to start and/or stop the device's operation, and/or perform one or more specified functions, such as to perform one or more punch advance motions, initiate graft counting, and/or perform other functions, as just some examples. In certain embodiments, some functions and/or setting selected by a switch, or other input device, may be operation for a particular portion of an operating cycle, and/or continue for one or more subsequent operating cycles, as just some examples.

In certain embodiments, control switches 22 may also allow a user to select and/or adjust one or more motion profiles, time-varying motion profiles, and/or movement parameters (motion profiles, time-varying motion profiles, and movement parameters are discussed in greater detail below). For example, control switches 22 may include one or more movement parameter input or adjustment buttons, or other input devices. Thus, control switches 22 may be utilized to select and/or adjust an operation condition for follicular dissection device 32, such as a particular time-varying motion profile and/or to select and/or adjust a speed, oscillation angle, and/or other movement parameters.

In certain embodiments, controller 12 may include one or more H-bridges. This particular embodiment depicts controller 12 having a plurality of H-bridges, H-bridge 20 and 21, such as may be used in where follicular dissection device 32 may have a plurality of drives, such as drives 34 and 36, for example. Of course, in certain embodiments, no h-bridge may be used; in other embodiments, any number of H-bridges may be used, without limitation. In the embodiment depicted in FIG. 8, H-bridges 20 or 21 may be used as low impedance switches to provide power to drives 34 or 36 of follicular dissection device 32 via a cable or other transmission device. Here, H-bridges 20 or 21 may be utilized, such as in connection with processor 14, to achieve various operating conditions, such as by providing pulse width modulated voltage to one or more drives of follicular dissection device 32, through H-bridge 20 or 21, as just an example. Such pulse width modulation, for example, may provide the effect of applying a lower voltage to one or more drives associated with follicular dissection device 32. For instance, in cases where controller 12 may be run off a 12-volt supply, a duty cycle may be set at 50% thereby creating a similar effect as though controller 12 were powered off of a 6-volt power supply at a 100% duty cycle, as just an example. Here, H-bridges 20 or 21 are merely examples of one type of voltage control device for a driver. Other control devices may include discrete transistors, analog power amplifiers, silicon controlled rectifiers, or relays, just as some non-limiting examples.

In certain embodiments, controller 12 may include display 24. As just an example, a display, such as display 24, may be capable of showing information about one or more movement parameters, such as a selected or current speed of a punch (e.g., RPM, oscillations per minute, vibrations per minute, and/or the like), an oscillation angle of a punch, one or more time-varying motion profiles, and/or the like, and/or showing a count of follicular extractions performed with follicular dissection device 32, such as a number of graft extracted for a particular operation cycle (e.g., one start/stop cycle). To illustrate this latter ability, as just an example, a count of follicular extractions may be derived based, at least in part, on a number of times a follicle is extracted for a particular operation cycle. For instance, if a follicle is extracted in a particular operation cycle, a switch (not depicted) which may be disposed with follicular dissection device 32 may be turned on to actuates a counter circuit to add a digit to a count. In certain embodiments, display 24 may be connected to mode switch 26 so a user can select which information may be displayed. In this example, mode switch 26 allows a user to select various options of information that may be displayed on display 24, for example, which may include a count of follicular extractions for a particular operation cycle. Thus, if mode switch 26 were selected to display a number of graft extracted for a particular cycle, display 24 may display a number of counts determined by the above-mentioned counter circuit, as just an example. In certain instances, a combined number of grafts extracted may be displayed, such as a total number of grafts for all operation cycles for a particular person, as just an example.

In certain embodiments, controller 12 may include an associated computing platform 28, such as a personal computer or a Programmable Logic Controller, as just some examples. Computing platform 28 may be connected to an input/output device (not depicted) of controller 12 directly, via a programmer 30, and/or may be connected in various other ways, such as RS232, RS48, CAN Bus, USB, Firewire, I2C, Ethernet, radio frequency, or infrared connection, as just as some examples. In certain embodiments, controller 12 may be directly connected to computing platform 28 via cable and may be driven from software loaded on computing platform 28. In another example, controller 12 may be initially programmed via computing platform 28 and/or programmer 30. Here, as just an example, a programmer 30 may be capable of inputting instructions into controller 12, such as to processor 14, for example. Such instructions may be stored in memory 16 accessible by controller 12. In such a case, computing platform 28 and/or programmer 30 may be disconnected from controller 12 and instructions stored on controller 12 may be delivered to or accessible by follicular dissection device 32, or other components or devices. In such a case, controller 12 may operate in a stand-alone mode. However, as another example, computing platform 28 may be connected for controlling and collecting information from one or more controllers 12. One such use for a connected approach may be for collecting information regarding the operation of a particular device, maintenance data, billing and accounting data, performance data, etc, just to mention a few.

As mentioned above, in certain embodiments, a user may select one or more motion profiles, time-varying motion profiles and/or movement parameters. In certain embodiments, one or more drivers of a follicular dissection device may drive a follicular extraction punch based, at least in part, on one or more motion profiles and/or one or more time-varying motion profiles. In this context, a motion profile comprises one or more programmed movement parameters, where movement parameters are constant for at least a portion of an operating cycle. Also, in this context, a time-varying motion profile comprises one or more programmed movement parameters, where at least one of the movement parameters varies as a function of time for at least a portion of an operating cycle. For instance, in certain embodiments, at least one movement parameter, such a speed, angle, stroke, and/or or distance, as just some examples, may be variable for at least a portion of an operation cycle. Likewise, a movement parameter may comprise information to drive one or more drivers of a follicular dissection device, such as speed information (e.g., RPM, oscillations per minute (OPM), vibrations per minute, etc), angle information (e.g., oscillation angle of a punch), distance information (e.g., distance a punch may extend and/or retract), and/or the like, associated with follicular extraction, as just some examples.

Figure 2:
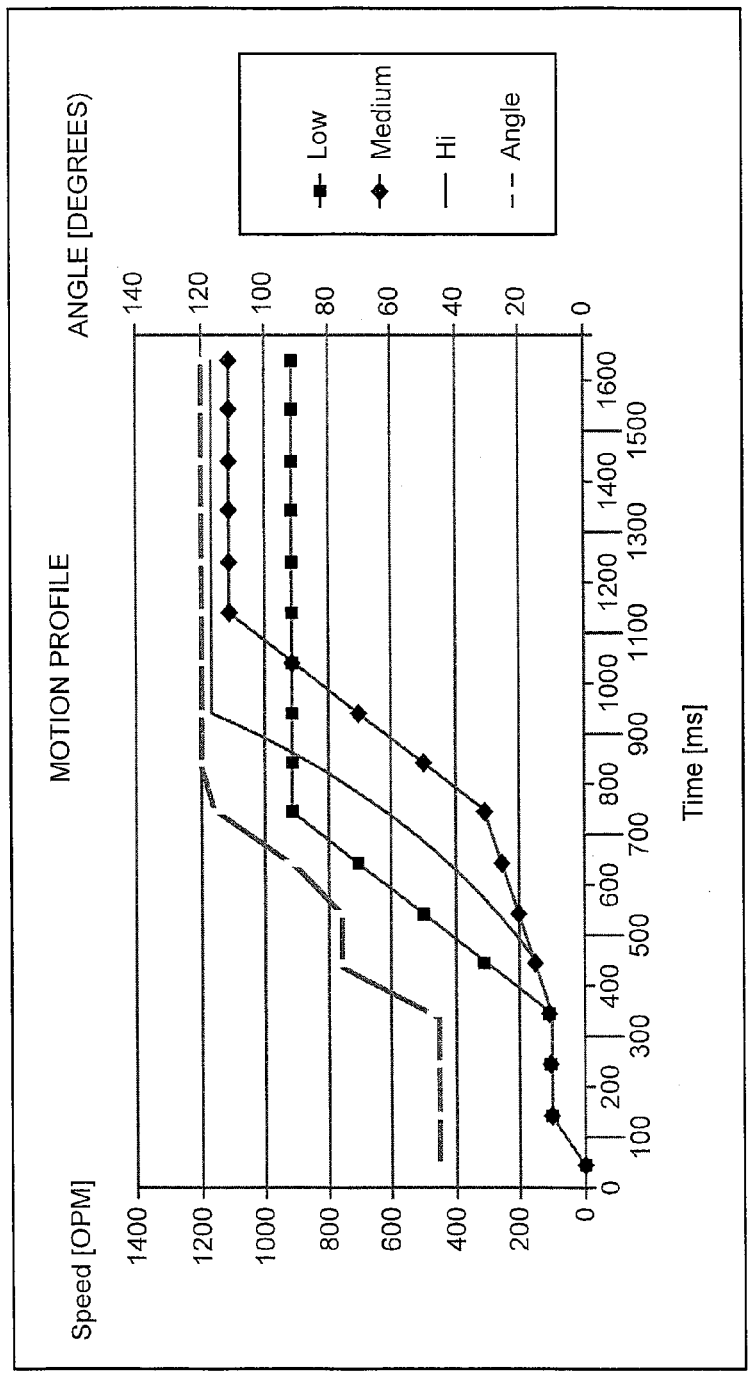
FIG. 2 is a graphical representation of exemplary motion profiles, in accordance with one or more embodiments.

FIG. 2, for example, depicts a graphical representation of various exemplary time-varying motion profiles. In certain embodiments, for example, one or more drivers of a follicular dissection device may be communicatively coupled to a controller and/or computing platform, such as previously described, to receive one or more control signals. Here, a control signal may represent and/or be based on information for one or more movement parameters (e.g., information to drive a driver, such as speed, angle, distance, etc.) which may be associated with one or more time-varying motion profiles. Such control signals may comprise voltages, analog signal values, binary digital signals, and/or other information, which may be used to instruct a particular drive of a follicular dissection device to rotate at a particular speed, at a particular angle, oscillate at a particular speed or distance, or extend and/or retract a particular distance, as just some examples. Thus, a time-varying motion profile may comprise any number of movement parameters, where at least one movement parameter varies with time for a portion of an operation cycle.

In certain embodiments, a controller, such as controller 12, may access, process, and/or apply one or more control signals to one or more drives of a follicular dissection device to, in turn, control movements of a punch. In certain embodiments, for example, a controller, such as controller 12, may access one or more movement parameters, which may be associated with a motion profile or time-varying motion profile. Here, for example, one or more movement parameters may comprise speed, angle, and/or distance information, such as represented in a table of values, accessible to controller 12. In this illustration, a controller, such as controller 12, may process these values to produce one or more control signals which may correspond to speed, angle and/or distance information. Accordingly, in certain embodiments, a controller, such as controller 12, may apply and/or transmit one or more such control signals to one or more drives of a follicular dissection device. These, control signals received and/or applied to one or more drives may enable one or more of drives to control movements of a punch, such as controlling a punch in accordance with one or more movement parameters which may be associated with one or more motion profiles and/or one or more time-varying motion profiles. Of course, this is merely an example and the scope of claimed subject matter is not limited in this respect.

Time-varying motion profiles may serve various functions. Suppose, for instance, it is desirable to prevent skin torsion or twisting during an initial contact of a punch with the skin of a patient. This may be desirable due to a torque on a punch, such as may be associated with a rotational cutting motion, for example, which may twist the skin as a result of the friction force between a punch and the tissue. Here, for example, friction may result in a graft dissected with an increased risk of transection. Accordingly, a time-varying motion profile may be designed and/or programmed to mitigate such risks. For example, one such motion profile is depicted in FIG. 2.

FIG. 2 is a plot of speed and angle of oscillation of a punch as a function of time. Here, the left Y axis depicts speed in oscillations per minute (OPM) of an oscillating punch. The right Y axis depicts angle in degrees of oscillation of a punch. Of course, values represented on these axes are only for illustrative purposes only. Accordingly, the scope of claimed subject matter is not limited to these exemplary values. The "low" motion profile in FIG. 2 will be now be described as just an illustrative example which may be used to decrease a risk of transection, just as described above. Here, for instance, the low profile depicts a low initial speed and angle in order to perform a scoring procedure (e.g., to first penetrate the skin). This may be illustrated in FIG. 2 as the "low" profile between approximately time zero and 350 milliseconds. Here, the "low" profile shows approximately a 45% angle of oscillation at the punch at roughly 100 oscillations per minute. Once a scoring is completed, a speed and/or angle may be automatically increased, such as corresponding to a particular motion profile, to perform the dissection and/or extraction procedure. Accordingly, the "low" profile in FIG. 2 shows that, after approximately 350 milliseconds, speed and angle parameters may increase to perform a dissection and/or extraction procedure.

Here, it should be noted that the manner or rate in which one or more movement parameters may vary as a function of time for a particular motion profile are nearly limitless. As some non-limiting examples, certain movement parameters, such as speed, may be constant, while others, such as angle and/or distance, may vary. One or more movement parameters may increase or decrease based on any number of functions, such as a linear function, a step function, an exponential function, and/or a combination thereof, as just some example. For example, a rate of increase or decrease of an angle and/or speed with time may initially follow a ramp function and, thereafter, a constant after scoring is completed, as just an example. Of course, an advantage of particular motion profile may be to tailor operation of a particular follicular dissection device for particular skin types or conditions, follicle characteristics, and/or the like.

In certain embodiments, one or more preprogrammed movement parameters associated with a time-varying motion profile may provide input into a controller, such as controller 12, in various ways. In certain embodiments, one or more preprogrammed movement parameters or settings may be created and stored in a computing platform, such as computing platform 28, and transmitted to controller 12. For example, one or more time-varying motion profiles may be stored in memory 16, allowing controller 12 to access such a profile and create various operating conditions. For instance, in certain embodiments, controller 12 may access or look up one or more movement parameters associated with a time-varying motion profile stored in memory 16, as just an example. In certain embodiments, one or more movement parameters associated with a time-varying motion profile may be stored in memory 16 as an array, a table, or a plurality of functions, equations, or values, as just some examples. To illustrate, suppose in a particular embodiment that a time-varying motion profile comprises speed information and distance information (e.g., dwell information). Here, this information may be stored in memory 16 corresponding to two slots in a table, one slot relating to speed and the other relating to distance. Such slots may define a voltage applied, a polarity of the voltage and/or a duration of the applied voltage, as just some examples. Furthermore, a number of slots may define a granularity or resolution of the control for a particular movement parameter, time-varying motion profile, or follicular dissection device. In certain embodiments, changing one or more values associated with a voltage, polarity, and/or time applied to one or more drivers may result in various operating characteristics, angles and/or speeds, as just some examples.

In certain embodiment, one or more simple or compound motions may be produced by a follicular dissection device based on one or more movement parameters to drive one or more drivers of a follicular dissection device, as just an example. For example, a processor 14 may access memory 16 and execute instructions causing drive assembly 34 or 36 of follicular dissection device 32 to execute one or more movements.

Figure 3:
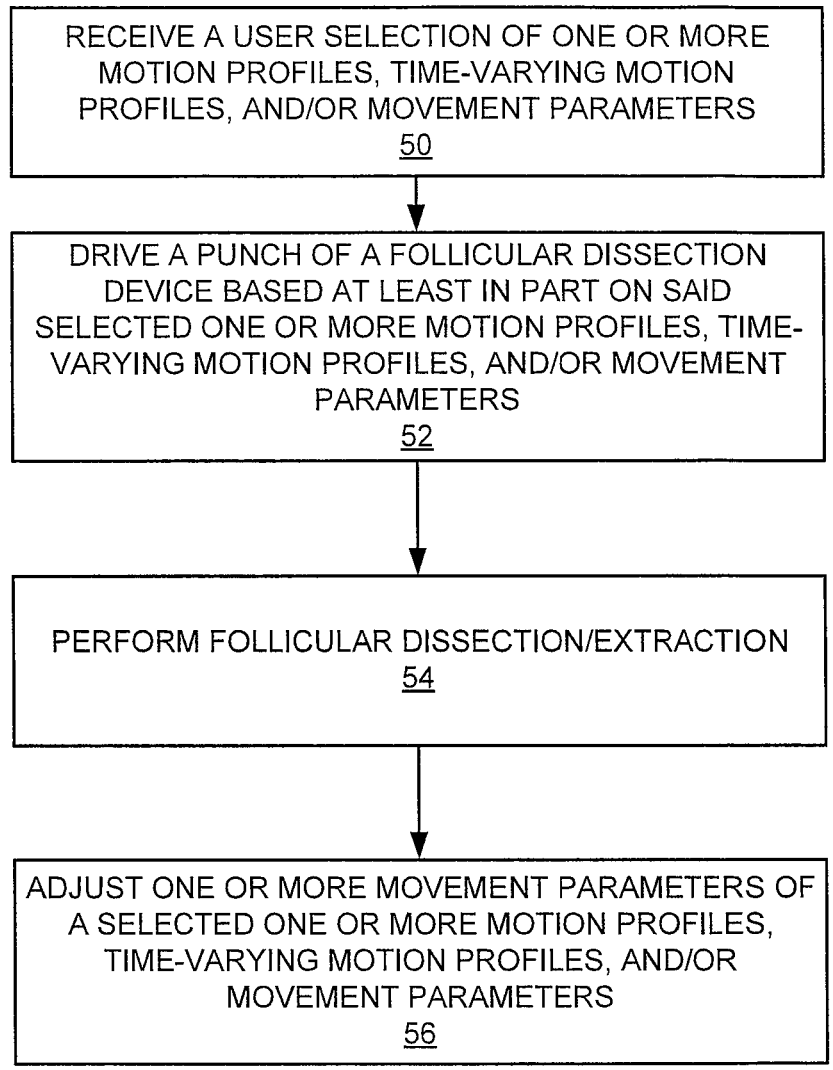
FIG. 3 is a flow diagram illustrating a method associated with a follicular dissection device in accordance with one or more embodiments.

FIG. 3 is a flow diagram illustrating a method for operation of a follicular dissection device in accordance with one or more embodiments. Various operations depicted in FIG. 3 may be used to control operation of a punch portion of a follicular dissection device in accordance with one or more embodiments, for example, although the scope of claimed subject matter is not limited in this respect. Additionally, although the exemplary operation shown in FIG. 3 comprises one particular order of blocks, the order in which the blocks are presented does not necessarily limit claimed subject matter to any particular order. Likewise, intervening blocks shown in FIG. 3 and/or additional blocks not shown in FIG. 3 may be employed and/or blocks shown in FIG. 3 may be eliminated, without departing from the scope of claimed subject matter.

One or more operations depicted in FIG. 3 may in certain embodiments be implemented in software, hardware, and/or firmware, and may comprise discrete operations. Exemplary hardware may comprise a microprocessor, a CPLD, or an FPGA, as just some examples. Additionally, one or more operations depicted in FIG. 3 may be implemented as a combination of one or all of the aforementioned components.

At block 50, a process or operation may be used to receive a user selection of one or more motion profiles, time-varying motion profiles, and/or movement parameters. In certain embodiments, for example, a particular motion profile, time-varying motion profile, and/or movement parameter may be selected from a plurality of motion profiles, time-varying motion profiles and/or movement parameters. At block 52, a punch portion of a follicular dissection device may be activated and/or driven based, at least in part, on such a selected profile and/or movement parameter.

As mentioned previously, a time-varying motion profile may include speed information, angle information, frequency information and/or stroke distance information as non-limiting examples, one or more of which may vary as a function of time, as just an example. Speed information and/or angle information may be associated with a rotational motion and/or an oscillation motion. In one example, speed information and/or angle information may vary over time from an initial speed and/or angle to a different resultant speed and/or angle over one or more intermediate speeds and/or angles. For example, such an initial speed may include a speed of 0-600 oscillations per minute and/or such an initial angle may include an angle of 0-90 degrees. In another example, such a speed may include a speed of 600-20,000 oscillations per minute and/or such a angle may include an angle of 90-360 degrees. In still another embodiment, only one parameter such as oscillation may vary with time while the speed may be kept at a constant speed. For example, an oscillation angle may vary from 0 to 90 degrees within 200 milliseconds while an oscillation speed may be maintained at approximately between 100 and 6,000 oscillations per minute. Additionally or alternatively, such a time-varying motion profile may include punch stroke distance information. Such information may be associated with an extension motion or a retraction motion. In one example embodiment, such punch stroke distance information may vary over time. For example, a punch advance motion may have a slow rate at first and advance a punch a particular distance, say about 1.0 mm, from a starting position to perform a scoring operation, then a rate of a punch advance may increase, such as to reduce the time associated with a follicular hair dissection/extraction procedure, as just an example.

At block 54, a follicular extraction procedure may be performed. During a follicular extraction procedure, a follicular extraction punch may be set to a reference or home position which may refer to a condition in which a tip of a punch just touches a scalp at a dissection site. During a procedure, a punch may be aligned with a hair angle while a cutting edge of punch may touch a surface of the scalp. After a switch is turned on, a punch may deliver a cutting motion. In certain embodiments, a punch advance motion may be performed manually, such as by pushing a punch forward until a depth stop touches the scalp, for example. A punch may then be withdrawn. Alternatively, in certain embodiments, a punch advance motion may be delivered automatically, such as described in more detail above. In such a case, if a switch activated, a punch may move back and forth between a surface of the scalp and deeper positions into the scalp until a desired depth is reached, such as where a depth stop may touch the surface of the scalp, for example. In such a case, a punch advance motion may reverse, pulling a punch backwards after dissecting a graft or to reposition a punch for another punch advance motion.

For a punch advance motion in an axial direction, a back and forth reciprocating (e.g., extension/retraction) motion may be performed, such as according to a time-varying motion profile. At the same time, such a time-varying motion profile may additionally govern a cutting motion (e.g., rotary motion, rotary oscillation motion, or an axial oscillation motion). As will be discussed below, in certain embodiments, a punch advance motion may be delivered by a variety of automated mechanisms, such as, for instance, by a solenoid actuator, a step motor, a voice coil, a pneumatic actuator, a hydraulic actuator, and/or the like. In a particular embodiment, such as a voice coil or solenoid actuator, as just some examples, a single drive may deliver a compound motion, such as a cutting and punch advance motion.

A punch advance motion may take place in a number of steps. For example, a punch may move back and forth in an axial motion with respect to a starting point. A starting point or a reference point may be when a tip of punch just touches a scalp. A punch in motion may move forward a particular distance with respect to a starting point and then move back to a reference position or home position. On a subsequent extension, a punch may move further forward and move back to a reference position. For example, a rotating or oscillating punch may contact the skin which would be a reference or zero position. Here, a punch may start to rotate, oscillate and/or vibrate and, in certain embodiments, a punch may also advance into the skin. For example, during such an advance, a punch may be inserted into the skin 0.5 mm, and then may move back to a reference position. Next, a punch may move deeper into the skin, such as a depth of 2.0 mm, and then may move back to a reference position, and again may move deeper into the skin, such as a depth of 4.0 mm and then move back to a reference position. This kind of stepped punch advance motion may allow the elastic tissue to relax to an unstressed position from the compressive stress exerted during an earlier feed motion. In certain embodiments, a rate of punch advance and retraction may be anywhere between 0 to 20,000 min/min, as just an example. At block 56, one or more movement parameters may be optionally adjusted during a follicular extraction procedure. For example, any number of steps, the sequence and the rate of such advances of punch, and/or the like, may be adjusted to desired values, such as through a selection of a time-varying motion profile, and/or an adjust of one or more movement parameters, as just an example.

FIGS. 4 through 10 are schematic diagrams of exemplary follicular dissection devices, in accordance with various embodiments. While what follows is a description of various exemplary components and/or configuration for a follicular dissection device these descriptions are merely examples of the follicular dissection devices encompassed within the scope of claimed subject matter. Thus, the scope of claimed subject matter is not to be limited by these examples or illustrations.

FIG. 4a is a cross-sectional schematic representation of an exemplary follicular dissection device 102, in accordance with an embodiment. As depicted in FIG. 2, drive assembly 106 may comprise one or more drives 110. A drive may comprise any device capable of producing or affecting movement, such as a motor, an actuator, and/or the like. For instance, in certain embodiments, a drive, such as drive 110, may include a direct current (DC) motor; a servo motor; a stepper motor; a solenoid actuator; a voice coil actuator; a pneumatic actuator; a piezoelectric actuator; and/or combinations thereof, as non-limiting examples. In certain embodiments, a drive, such as drive 110, may be operable to produce and/or generate speeds which may be between approximately 0 and 20,000 rpm (or oscillations per minute, strokes per minute, etc.). In addition, a drive, such as drive 110, may be operable to produce and/or generate an oscillation angle between approximately 0 to 360 degrees.

In this embodiment, drive 110 of follicular dissection assembly 102 may comprise a main motion source for follicular dissection device 102, such as a motor or actuator, as non-limiting examples. Accordingly, drive 110 may be operable to perform one or more motions associated with follicular dissection and/or extraction, such as providing force to move follicular extraction punch 108 in one or more simple or compound motions, as non-limiting examples. Thus, for example, drive 110 may be operable to perform one or more motions, such as rotate, reciprocate, vibrate, oscillate, and/or the like, and/or combinations thereof, as yet another example. Various embodiments with different drive(s) will be explained in more detail below. First, however, to illustrate an exemplary coupling and interplay between one or more components of driven assembly 104 and drive assembly 106, a more specific implementation of the embodiment depicted in FIG. 4a is laid out below.

For ease of illustration, in this particular embodiment, drive 110 of follicular dissection device 102 comprises a single DC motor. Here, drive 110 may be coupled to output shaft coupling 112 via drive shaft 114. Thus, drive 110 may be coupled to driven assembly 104. For example, driven assembly 104 and drive assembly 106 may be removably attached to one another. In such a case, driven assembly 104 may be connected to drive assembly 106 such that a quick assembly and disassembly may be possible by assembling front housing 126 to drive housing 111. In this embodiment, output shaft coupling 112 of drive assembly 106 may be operatively associated with punch holder coupling 116 of driven assembly 104.

Continuing with this illustration, as depicted in FIG. 4a, driven assembly 104 may comprise a follicular extraction punch 108. For example, driven assembly 104 may include a punch holder 118. For example, all or portions of driven assembly 104 may be the same or similar to corresponding structures described in previous USPTO Patent Publication no. 20060178678 and Patent Publication no. 20070293884. However, these are merely examples of such structures and claimed subject matter is not limited in this respect. In certain embodiments, barrel tip 124 of barrel 129 may be used as a depth stop for punch tip 122 of punch 108. Such a depth stop may be capable of restricting a punch advance motion, where follicular extraction punch 108 may be pushed forward until depth stop 124 touches the scalp, as just an example. Barrel 129 may be coupled to front handle 126, such as by a threading connection, which may allow adjustment of depth of a punch protruding out of barrel tip 124. Punch holder 118 may be fixedly coupled to punch 108 and punch holder coupling 116. Punch holder 118 may and/or punch shaft coupling 116 may be sealed with respect to a front housing 126 of driven assembly 104 by using a swivel 128. Swivel 128 may be fixedly coupled to front handle 126 while allowing free movement of punch holder coupling 116 and provides a fluid seal with O-rings 127, for example. For example, such swivel and O-rings may be capable of preventing fluid communication between follicular extraction punch 108 and drive assembly 106.

As mentioned above, drive 110 of follicular dissection assembly 102 may comprise a main motion source for follicular dissection device 102. In certain embodiments, particular drives may have particular control techniques. For instance, in certain embodiments, drive 110 may comprise a DC motor. Here, a DC motor may be controlled differently from other types of motors or actuators, such as a servo motor, for example, since a DC motor may have no position feedback, as just an example. Similarly, a stepper motor may have no position feedback; however, a controller, such as controller 12, may track one or more movements of a stepper motor since it may rotate in fixed step sizes. In certain embodiments, as just an example, a DC motor may receive power from an H-bridge. As described above, in certain embodiments, an H-bridge may be set to cause the motor to rotate in a particular direction, such as clockwise or counterclockwise. A controller, based on a particular motion profile and/or movement parameter, may instruct a DC motor to rotate in a clockwise and counterclockwise direction over some specified arc angle in degrees. At the end of an arc, a break function may be applied to cause a faster stop and restart in the opposite direction. Thus, a dc motor may be controlled simply by applying a specific voltage and polarity to an armature for a specific period of time and reversing that voltage. In such a manner, a DC motor drive may produce punch motions corresponding to one or more time-varying motion profiles. Of course, other types of motors, such as a servo motors and/or a stepper motor may produce punch motions which may correspond to one or more time-varying motion profiles in a similar manner.

In certain embodiments, a position sensor may be attached to DC motor shaft 114, for example. For convenience, such a DC motor coupled with a position sensor may be referred to as a servomotor; though, of course, this is merely an example and claimed subject matter is not limited in this respect. As depicted in this particular embodiment, a position sensor may be optical encoder 113, as just an example. In certain embodiments, electrical power may be supplied to a position sensor from a controller. Also, a feedback signal, such as described previously, may be delivered from a position sensor, such as optical encoder 113, to a controller, which may allow a controller to determine a speed, angle, and/or direction of a drive, as just an example. Of course, in certain embodiments, other types of position sensors may be used. For example, in certain embodiment, a non-optical encoder may be used where a voltage level or polarity may be adjusted as a function of encoder signal feedback to achieve a desired angle and/or speed, as just an example. Of course, as mentioned previously, in certain embodiments, a position sensor may not be used. As just one example, in the application of stepper motor, various individual steps of a servo motor may be controlled, where information about direction, speed and/or angle may be generated or monitored by a controller. Here, for example, a controller may generate individual steps and, as a result, no position sensor may be used since no position feedback may be desired.

As suggested previously, the above description of the embodiment depicted in FIG. 4a is merely exemplary of particular components and/or a particular configuration for those components for follicular dissection device 102. Accordingly, the scope of claimed subject matter is not to be limited to exemplary components or configurations depicted described herein. Examples of just a few other components or configurations are explained in more detail below. Here, however, it is noted that certain details which may or may not have been described above may be omitted so as to not obscure claimed subject matter.

FIG. 4b, for example, depicts one exemplary component which may be utilized with a follicular dissection device 102 in FIG. 4a. Here, as just an example, FIG. 4b illustrates just one of a number of components which may be utilized to convert various motions. Suppose, for instance, a drive associated with a particular follicular dissection device may be operable to produce only rotary motion. Here, it may be desirable to convert rotary motion to achieve an oscillating motion, as just an example. For instance, oscillating planetary gear assembly 162 may comprises ring gear 164, sun gear 166, planet gear 168, input shaft 170, and output shaft 172, as just some sample non-limiting components. As depicted in FIG. 4b, ring gear 164 and sun gear 166 have a certain number of gear teeth removed such that the planet gear may couple gears with either ring gear 164 and/or sun gear 166 at particular times. Thus, a coupling of the aforementioned gears may be intermittent, such that if ring gear 164 couples with planet gear 168, planet gear 168 may rotate in one direction, and if ring gear 164 is not coupled with planet gear 168, sun gear 166 may be coupled with planet gear 168 such that planet gear 168 is rotated in a reverse direction.

Here, as just an example, an output shaft of a DC motor may be coupled to input shaft 170 of ring gear 164 and/or sun gear 166. Thus, such a motor may drive, such as rotate, ring gear 164 and sun gear 166 in a particular direction. Such a rotational motion may be converted into an oscillation motion by a oscillating planetary gear assembly as described above. Thus, output shaft 172 may be coupled to a driven assembly via a shaft coupling and punch holder as described in FIG. 4a. Thus, oscillation motions may be produced at a punch for a rotary drive. Of course, this is merely one example of a device which may be used in to convert one or more motion produced by a drive associated with follicular dissection and/or extraction. Accordingly, claimed subject matter is not limited in this respect.

FIG. 5a, for example, depicts exemplary follicular dissection device 302 operable to use a piezoelectric drive, such as piezoelectric actuator 310. In certain embodiments, piezoactuator 310 may be comprised of a flexing or bending type piezoactuator. A flexing or bending actuator may produce mechanical deflection in response to an electrical signal. For instance, in certain embodiments, two or more strips of piezoelectric ceramic may be bonded together and electrically connected in parallel. Here, if an electrical input is applied, one ceramic layer may expands and the other may contract, which may result in an actuator flexing to a particular side, as just an example. Here, altering a polarity of an applied voltage, may result in an actuator flexing to another side, as just an example. In one particular embodiment, a multi-sheet/plate transducers may be referred to as benders, bimorphs, or flexural elements. In certain embodiments, frequency and/or stroke of a piezoactuator may be controlled by an amplitude and/or frequency of a voltage, such as may be supplied from a controller, as just an example.

As some non-limiting examples, depending on the type of piezo sensors used, a piezoactuator may produce motion such as reciprocating, vibrating, rotating and/or oscillating motions. A follicular dissection device, such as device 322, may be capable of producing various movements associated with follicular extraction using a piezoactuator, such as piezoactuator 310. The piezoactuator may also provide movements in a "transverse" direction (e.g., perpendicular to an axis of polarization). In such embodiments where layers of piezo sensors are used, at one end, one or more piezo sensors may be fixed with a housing from any motion at the fixed end 319, while another end is free, flexing end 321 of the actuator, as just an example. In a particular embodiment, if voltage is applied to one layer of piezoactuator 310, and not to an adjacent layer, a layer to which voltage was applied may extend or contract relative to the adjacent sensor, thus pulling or bending the actuator to one side or the other. The flexing end 321 therefore deflects or moves to one side or the other.

Here, for example, a lateral vibration may be obtained at a flexing end 321 connected to link arm 320. Alternatively, an oscillating cam, such as swivel disc 330, may be slidably attached to link arm 320 and also attached to the centre of the housing with a rotating connection. Here, link 320 attached to the free end of piezoactuator 310, may move laterally to one side and/or the other with the frequency of the source voltage. Also, link 320 may slide inside a vertical slot provided in swivel disc 330, which may provide force to swivel disc 330 to oscillate about the longitudinal axis of piezoactuator 310. Here, swivel disc 330 may be coupled to a shaft coupling to transmit a motion to the punch assembly. The oscillating motion from the coupling 312 is transferred to the punch 308 through punch holder coupling 317 and punch holder 318.

In certain embodiments, a piezoacutuator drive assembly may utilize disc type piezosensors. One such assembly is depicted in FIG. 5b, as just an example. In such a piezoactuator arrangement, an electric field may be placed across a thickness of a sheet of piezoceramic, allowing a stack to expand and/or contract in the thickness or axial direction (e.g., along an axis of polarization). Here, as just an example, one or more electrodes may be placed substantially between one or more discs so that such discs may be energized by a controller.

In FIG. 5b, various components are depicted which may be associated with a device driven by a piezoelectric drive. As just one example, the view depicts an exemplary portion of an assembly which may be used with a piezoactuator drive assembly enclosed in housing 362. For example, an exemplary piezo-stack 360 is depicted, which may be used to move punch holder 352 and thus a punch may oscillate in an axial direction. In certain embodiments, a motion in an axial direction may be small (on the order of tens of nanometers). Thus, piezo-stack 360 may comprise a number of piezo-discs assembled into one monolithic structure to obtain larger displacement for practical applications. In certain embodiments, a frequency and/or stroke of a piezoactuator may be controlled by an amplitude and/or frequency of a voltage supplied from a controller through power line 365, as just an example.

For example, a vibrating motion along an axis of a piezoactuator may be used for a vibration type motion at punch 308. In certain embodiments, one or more punches used with such axial oscillation may be pointed serrated tips that may enable cutting with less force. Here, for example, one or more pointed tips associated with such punches may be inserted in to a scalp with little force and allow for a more continuous dissection of the scalp, as just an example. Of course, one or more other types of punches may be used and claimed subject matter is not limited in this respect. In certain embodiments, barrel 353 may be adjustably coupled to housing 362. Here, barrel 353 may partially cover punch tip 351. The punch tip exposed partially from the tip of the barrel 353 may be inserted in to the scalp and the tip of the barrel is used as a depth stop.

Figure 6:
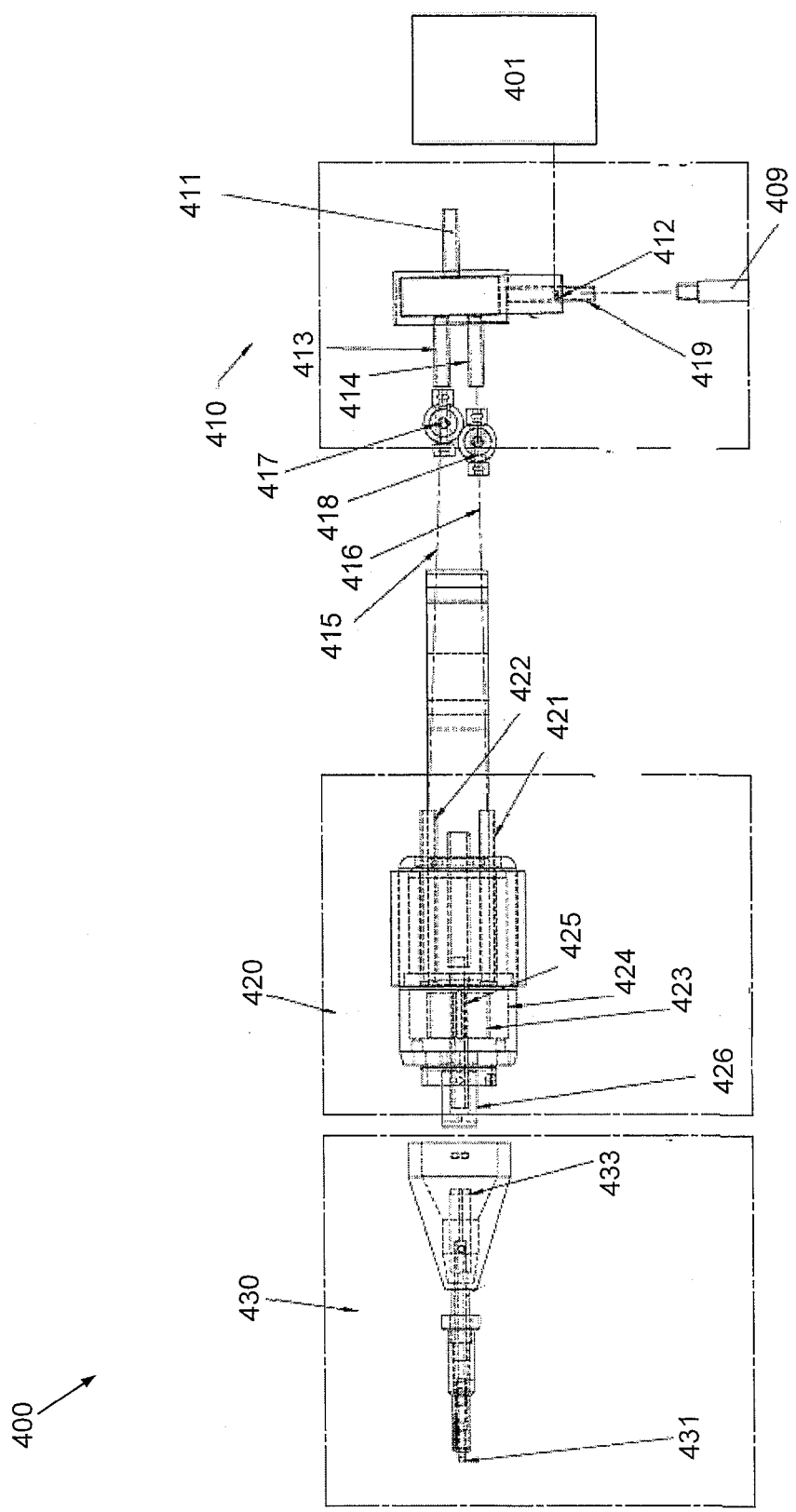

FIG. 6 depicts an exemplary follicular dissection device 400 wherein a drive may comprise a pneumatic actuator. Here, for instance, a pneumatic actuator may be used to impart one or more motions, such as rotary and/or oscillation motions, to a punch. Generally, motions, such as an oscillating motions, may be generated by pneumatic actuators using a rack and pinion assembly so as to convert a linear motion to rotary motion or by using a rotary vane actuator, as just some examples. In a case of a rack and pinion assembly (not shown), a cylinder and piston at each end of a rack drive may move a punch back and forth in an axial direction while a pinion may move a punch in a rotary or oscillation direction about a punch's axis. In certain embodiments a pinion shaft may be directly coupled to a drive shaft of a driven assembly. Below, an application of a rotary vane actuator is discussed.

FIG. 6 shows a schematic representation of a pneumatic actuator assembly 400 comprising a solenoid valve assembly 410, a pneumatic vane type rotary actuator assembly 420, and driven assembly/punch assembly 430. In certain embodiments, pressurized air from a compressor, reservoir and air dryer (not shown) may be delivered through a pressure regulator (not shown). A pressure regulator may be used to limit a maximum air pressure delivered to the valve. An air dryer (not shown) may remove water vapor from the air. Dry, compressed air may then be fed to the inlet port 411 of a solenoid valve 410. A voltage to activate a solenoid may be delivered to connection 412 by controller 401. Two tubing connections 415 and 416, are depicted running between two ports 413 and 414, of the solenoid valve and two ports 421 and 422, of pneumatic actuator 420. Speed control valves 417 and 418 may be installed along lines 415 and 416. Such valves may be check valves (e.g., needle valves limiting the opening of an orifice) installed before the pneumatic vane actuator 420 so that compressed air flow rate allowed in to the actuator compartment may be controlled to control an oscillating speed of vane 423 and thus of a punch 431. In certain embodiments, one or two exhaust ports 419 on solenoid valve 410 may be connected to tubing that run to a silencer 409, or silencers placed far away from the application area, to limit noise of the exhaust air.

In certain embodiments, one or more rotary pneumatic vane type actuators may convert pneumatic pressure into rotary motion. Rotary pneumatic vane type actuators may comprise single vane or double vane actuators. Rotary pneumatic vane type actuators may comprise a cylindrical chamber with two ports separated by stationary barriers 424. A vane, such as vane 423, may be connected to a drive shaft 425 between the barriers. Differential air pressure applied across the vane may rotate vane 423 and thus drive shaft 425 until the vane meets the barrier 424. Rotation may be reversed by reversing pressure of fluid at the inlet and outlet ports by the action of solenoid valve 410, as just an example. Such pressure may be controlled by controller 401.

In certain embodiments, a control signal may be sent from controller 401 to directional solenoid control valve 410. In one embodiment, for example, actuator output shaft 425 may be coupled to output shaft coupling 426 which, in turn, may be coupled to a punch holder coupling 433 of the driven assembly 430 and punch 431. Thus, any oscillation from pneumatic actuator 420 may be transferred to punch 431. As just an example, here a speed of oscillation may be controlled by controlling a duration and frequency of a voltage applied to a solenoid valve and by limiting a flow rate of the compressed air using the speed control valves 417 and 418.

Figure 7:
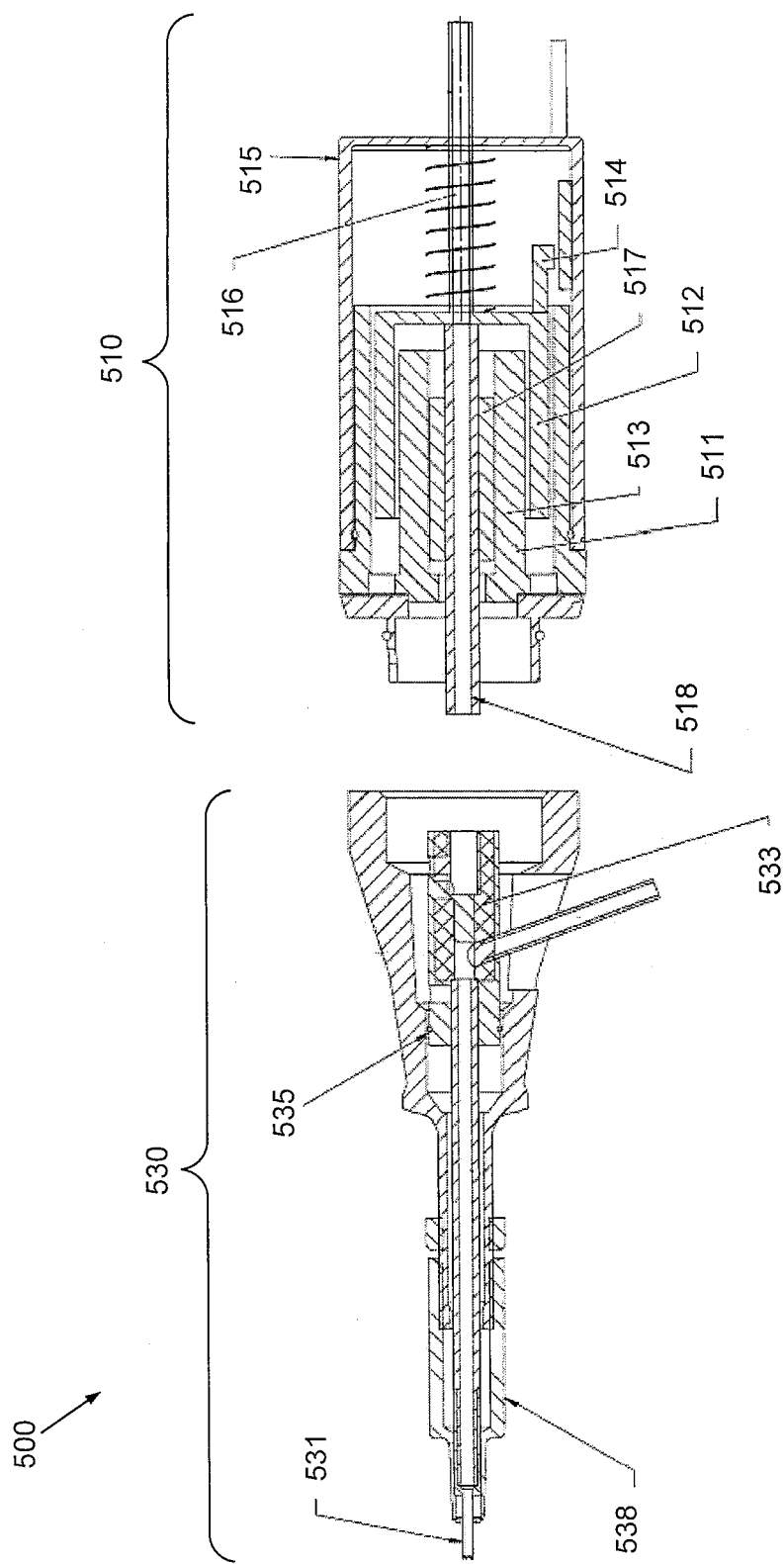

FIG. 7 depicts exemplary follicular dissection device 500 wherein a drive may comprise a voice coil actuator 510 and a driven assembly 530. In this embodiment, linear voice coil actuator 510 comprises a field assembly 511 with a cylindrical magnet located that defines a circular gap between the cylindrical magnet and coil assembly 512, a coil assembly positioned in the circular gap that rides over a core 513 positioned at the center of the field assembly. Output shaft 518 of coil assembly 512 may ride over bearing 517 located inside core 513. A home position of coil assembly 512 may be maintained with spring 516. In certain embodiments, a voice coil actuator may additionally comprise a sensor assembly 514 and a housing 515.

In certain embodiments, a voltage applied to coil assembly 512 may power an electromagnetic field which interacts with a magnetic field of the field assembly 511. Such an interaction may create a force that pushes or pulls the coil assembly depending on the polarity of the voltage applied. Generally, in a voice coil actuator, movements in various directions may be obtained by varying a magnitude and direction of a current applied to the coils, such as from a controller, for example.

In certain embodiments, motions produced by a voice coil may be axial or rotary, depending on the type of the voice coil actuator. In certain embodiments, for example, a voice coil may operate similar to a servo motor. Of course, a voice coil, such as voice coil actuator 510, may be capable of producing various movements associated with follicular extraction, such as vibration, extension, reciprocation, and the like, as non-limiting examples. As an example, a voice coil actuator may be used to oscillate axially to produce a cutting motion and also produce a superimposed punch advance motion, as just an example. Accordingly, a single voice coil actuator may produce a compound motion, as just an example. For example, a controller may send signals to produce a compound motion such that coil assembly 512 may vibrate at a certain frequency and also travel in the axial direction to a predetermined distance and come back to a home position. A frequency of oscillation may be varied by the controller to provide particular movements, such as in accordance with one or more motion profiles, time-varying motion profiles and/or movement parameters, for a particular follicular dissection procedure. Punch 531 in driven assembly 530 may be coupled to the coil assembly through the punch holder 531 and shaft couplings 533. In this way, motions of coil assembly 512 may be transferred to punch 531.

Also, FIG. 7 depicts position sensor 514. To be clear, one or more position sensors may be employed in any embodiment, and thus its depiction and description with reference to FIG. 7 does not imply that it is specific to that embodiment, nor to any other embodiment.

For instance, a position sensor was mentioned previously with reference to FIG. 5, for example. As mentioned previously, in certain embodiments, a position sensor, such as position sensor 514, may be used to provide one or more position feedback signals to a controller, computing platform, and/or other device or component. Here, in this embodiment, a position sensor, such as a linear position sensor, may provide information about a position of coil assembly 512, such as voice coil actuator 510, and in turn a position or orientation of a punch, such as punch 531, to a controller, a computing platform, and/or other processing device, for example.

For instance, with reference to the embodiment depicted in FIG. 7, position sensor 514 for a voice coil actuator may comprise one or more of various types of sensors. For instance, in certain embodiments, position sensor 514 may comprise an incremental linear optical encoder, a linear sliding potentiometer, a linear Hall Effect Sensor, and/or a Linear Voltage Displacement Sensor (LVDS), just some examples. In the case of an LVDT position sensor, an output signal may be analog. Thus, voltage levels on these analog inputs may be proportional to a position of a voice coil, as just an example. Of course, in other embodiments, one or more other types of position sensors may be used. To illustrate how feedback signals may be used, in this embodiment, a controller may analyze a position feedback signal and may adjust a control signal for the next position of voice coil assembly 512 and/or a punch. Here, a controller thus assigns signal voltage and current to a voice coil instructing it to assume various positions.

Figure 8:
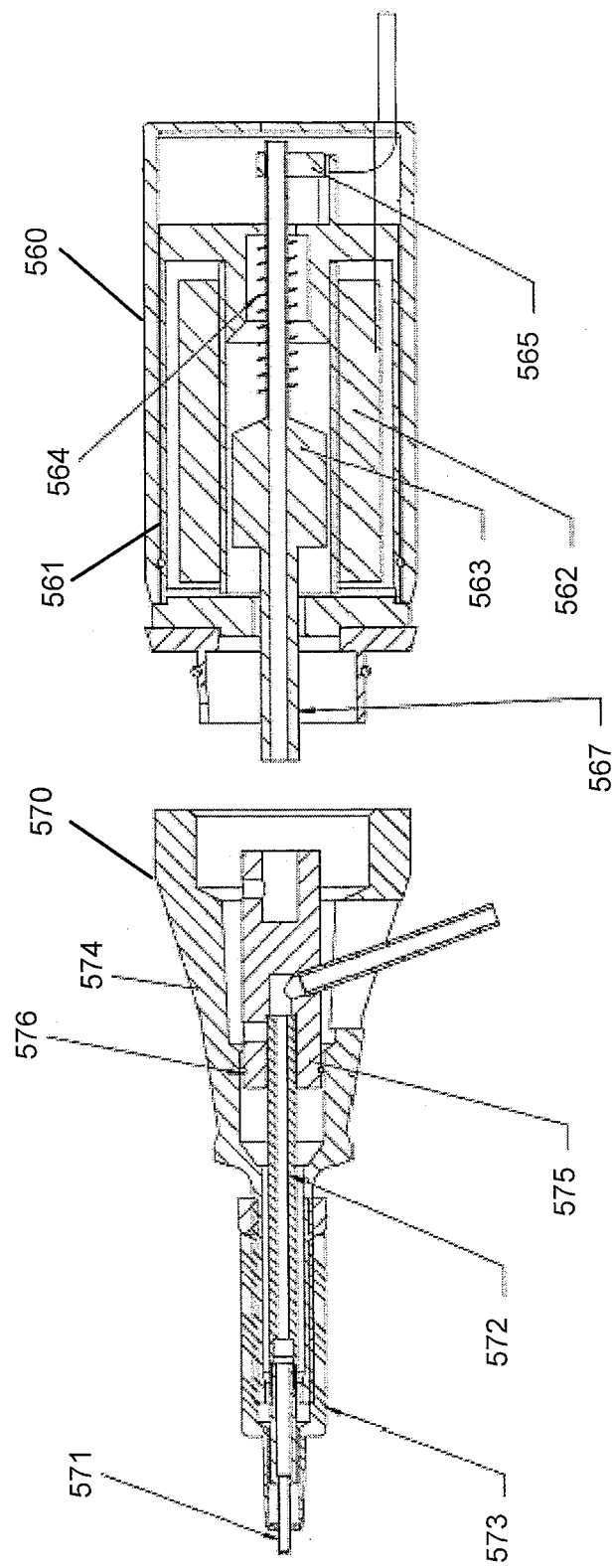

FIG. 8 depicts exemplary follicular dissection device 500 wherein a drive may comprise a solenoid actuator. Here, exemplary follicular dissection device 500 may comprise a drive assembly 560, solenoid actuator 561, and a driven assembly 570. Drive assembly 560 may be connected to driven assembly 570 where output end 567 of plunger 563 is connected to punch holder coupling 575 which, in turn, may be connected to the punch holder 572 and punch 571. As described above, driven assembly 570 may comprise a barrel 573 and front handle 574. Punch holder coupling 575 has a seal connection with front handle 574 by means of a wiper seal 576 which may allow an axial movement but prevents fluid communication.

In this embodiment, a magnetic field may be created in coil 562. Plunger 563 represents an inner shaft of a solenoid. Here, a magnetic field may apply a force to plunger 563, either attracting or repelling it. If a magnetic field is turned off, a reaction or returning motion may be created. In certain embodiments, this reaction motion may be produced by spring 564. In certain embodiments, an applied voltage, such as may be controlled or produced by a controller, may determine movement of plunger 563. Accordingly, in this manner, axial motions of a punch may result.

For example, a controller may be used to apply a voltage to a solenoid, such as using pulse width modulation, as previously mentioned. Here, plunger 563 may be connected in series with a position sensor 565, such as a potentiometer, where the one part is attached to the plunger shaft and the other to the stationary housing, for example. For solenoid actuator 561, a driving power may be supplied through an H-bridge via a controller.

In certain embodiments, two solenoids may be connected, such as in series, by fixedly coupling the plunger tips. Here, two solenoids may be driven independently by the controller. In certain embodiments, if one solenoid is powered and the other one is not, the energized solenoid may apply force on the other plunger. In certain embodiments, two solenoids may be powered one at a time to produce an oscillation in an axial direction. This configuration may produce an axial vibrating motion on a punch, as just an example. In still another embodiment, two solenoids may be connected by fixedly coupling the plunger tips. For example, a first solenoid may be energized with a constant voltage such that a plunger may be positioned towards a center of a coil. A second solenoid may be energized with a pulse modulated signal to provide a vibrating motion to the punch. This later solenoid may act against the first solenoid which may act as an electronic spring. Here, varying a constant voltage may vary a voltage on a solenoid acting as a spring. This combination may prevent plungers from impacting against one or more stop plates. Alternatively, two solenoids may be energized in series so that the force obtained may be increased.

Figure 9:
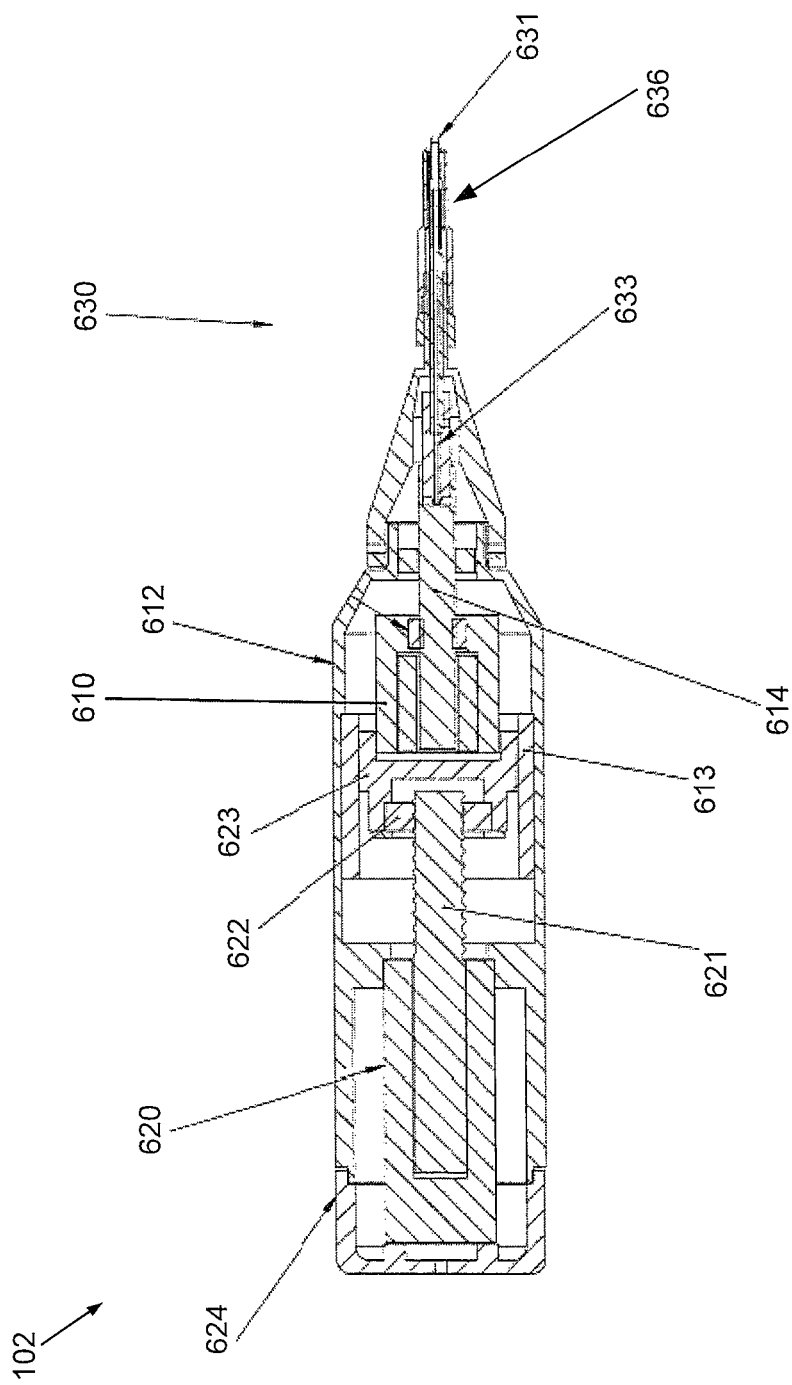
Figure 10:
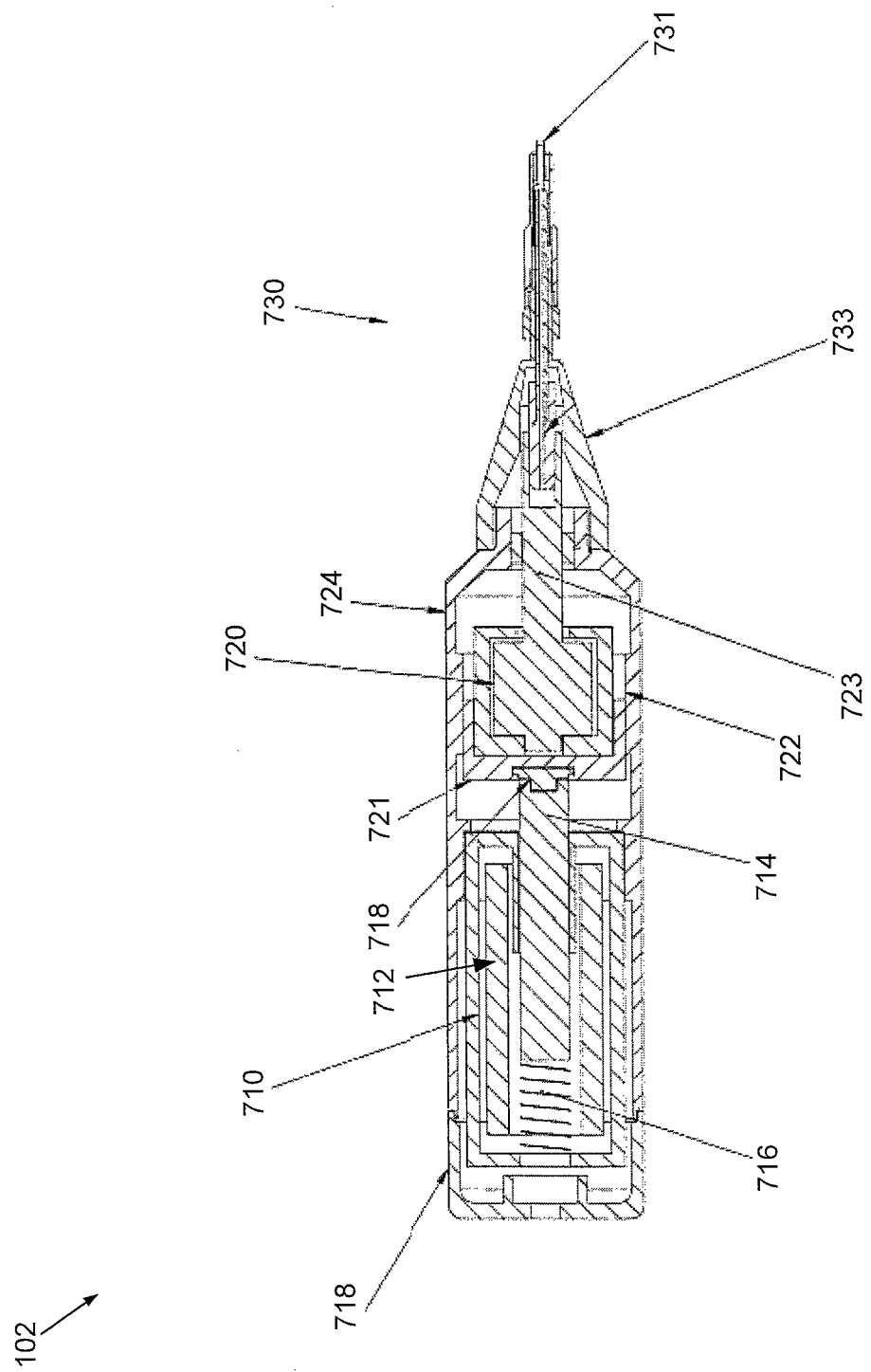

As yet another example, FIGS. 9 and 10 depict schematic representation of an exemplary follicular dissection device where a drive assembly comprises a plurality of drives. For instance, in certain embodiments, a first drive may deliver a cutting motion, such as a rotational motion, a vibration motion and/or an oscillation motion, to a punch while a second drive may deliver a punch advance motion, such as an extension motion, a retraction motion, a vibration motion, and/or a reciprocating motion. Alternatively, one or more cutting motion may be obtained from two drives while a punch advance motion may be delivered manually, as just an example. Similarly, two or more drives may provide both one or more cutting motion and one or more punch advance motions, as yet another example.

FIG. 9, for example, depicts a follicular dissection device 102 with a dual-drive. In this embodiment, drive one comprises a stepper or DC motor 610 and drive two comprises a stepper/motor actuator 620. In certain embodiments, drive one and drive two may be controlled independently from a controller, such as controller 12 in FIG. 1. For instance, a controller may send a control signal to drive 610 to instruct it to perform an oscillating cutting motion at a particular angle and/or speed. Likewise, a controller may send another control signal to drive 620 to instruct it to perform a punch advance motion at a particular distance and/or speed, as just an example.

Of course, it is noted that the types of motors depicted in this embodiment are merely exemplary and, accordingly, do not limit the scope of claimed subject matter. Various types of drives may function in combination in a plurality of drive configurations to produce one or more motions associated with follicular extraction. Thus, as just an example, one or the two drives depicted in FIG. 9 may comprise a DC motor, a servo motor, a stepper motor or solenoid, a voice coil actuator, a pneumatic actuator and/or a piezoactuator, as non-limiting examples.

In certain embodiments, one particular drive of a multi-drive device may deliver a punch advance linear motion. While a single drive of a follicular dissection device may produce only rotary motion, various mechanisms may be added to convert a rotary motion to a linear axial motion, to perform cutting and/or punch advance, for example. To illustrate, in FIG. 9, suppose stepper motor 620 enclosed in housing 612 and 624 produces a rotary motion. Here, this motion may be converted to a linear motion with screw 621 and nut 622. Screw 621, for example, may be rotated with the stepper motor 620. Here, nut 622 may be coupled to screw 621 and be constrained to move only in the axial direction, such as due, at least in part, to a coupling with motor adaptor 623, for example. Thus, nut 622 may move only in the axial direction back and forth depending on the direction of rotation of screw 621. In certain embodiments, motor adaptor 623 may be free to move in the axial direction on bearing surface 613. For example, drive 610 may be fixedly connected with motor adaptor 613 while it is free to move along the axial direction in housing 612. Thus, drive one may move back and forth with nut 622 while delivering a cutting motion.

In certain embodiments, drive 620 may move a punch back and forth in an axial direction to perform a punch advance motion, while drive 610 may perform any of the cutting motions described earlier. Therefore, punch 631 in driven assembly 630 may receive one or more cutting motions from drive 610 and a punch advance motion, which may be superimposed over one or more axial cutting motion, from drive 620. Here, output shaft 614 may be coupled to output shaft coupling 633 which may be coupled to punch 631 through punch holder 636.

As suggested above, in FIG. 9 a dual-drive configuration is depicted where either drive one or drive two may comprise a stepper motor. In general, a stepper motor is a brushless, synchronous electric motor which may divide a full rotation into a large number of steps. A position of a drive motor may be controlled precisely, without any feedback mechanism (e.g., open-loop controller). A stepper motor may comprise multiple "toothed" electromagnets arranged around a central gear-shaped piece of metal.

The electromagnets may be energized by an external control circuit, such as via a controller, computing platform, and/or other device. To make a motor shaft turn, a first electromagnet is given power, which makes the gear's teeth magnetically attracted to the electromagnet's teeth. If the gear's teeth are aligned to the first electromagnet, they may be slightly offset from the next electromagnet. Thus, if the next electromagnet is turned on and the first is turned off, the gear rotates slightly to align with the next one. Each of those rotations may be referred to as a "step". In that way, the motor can be turned by a precise angle.

In certain embodiments, drive one, such as stepper motor/DC motor 610, may provide a cutting (e.g., dissection) motion, such as a rotating and/or oscillating motion, for example. In certain embodiments, individual steps of a stepper motor may be determined by a controller, a computing platform, and/or other device, such as where such a device generates a number of steps, and/or a dwell time, and provides a control signal to a stepper motor. Thus, in certain embodiments, a stepper motor may not have a position sensor, since no feedback may be desired. In this instance, however, a position sensor may be used to provide information to a controller or other processing device about punch direction and angle, as just an example. In certain embodiments, drive two, such as stepper motor/actuator 620, may provide a punch advance motion, such as a vibrating and/or reciprocating motion, as just an example. Of course, as mention previously, in certain embodiments, a punch advance motion may be performed manually.

Similar to the embodiment depicted in FIG. 9, FIG. 10 depicts a follicular dissection device 102 with a dual-drive. In this embodiment, however, drive two comprises solenoid actuator 710. Here, solenoid actuator 710 may comprise coil 712, armature or plunger 714 and spring 716 enclosed in housing 724 and 718. In this embodiment, solenoid actuator 710 may produce a punch advance motion. For instance, solenoid actuator 710 may be positioned in proportion to a voltage applied. In certain embodiments, for example, if coil 712 is energized, a force applied to the armature/plunger may be proportional to a change in inductance of the coil with respect to the change in position of the armature, and the current flowing through the coil. Thus, the force applied to the armature may move the armature in a direction that increases the coil's inductance. A voltage applied to the coil may result in the solenoid actuator moving in or out towards the centre of the coil in an axial motion (e.g., punch advance motion). In certain embodiments, this motion may be performed against an extension spring 716, which may return a plunger back to a starting position if a coil is de-energized.

In this embodiment, a plunger tip may be coupled to motor adaptor 721, thus pushing or pulling drive 720 in the axial direction along bearing surfaces 722. Similar to embodiments previously described, drive one 720 may perform any cutting motions while a punch advance motion may be produced by drive 710. Of course, in certain embodiments, any drive of a number of drives may produce one or more cutting motions, one or more punch advance motions, and or combinations thereof.

Here, output shaft 723 from drive 720 may be coupled to punch 731 in driven assembly 730 by means of output shaft coupling 731. Front handle 733 of driven assembly 730 may be coupled with housing 724 of drive 720.

Returning to FIG. 4a, various follicular dissection devices, such as those described above, may be associated with various components to perform a wide variety of functions. In certain embodiments, for example, a follicular dissection device may include a one or more irrigation (e.g. fluid), aspiration and/or cooling lines. For example, cooling line 130 may be capable of transmitting coolant to a follicular dissection site. To illustrate, during a procedure, follicular extraction punch 108 may generate heat due to friction, such as may be produced with high speed rotational and axial motions contacting and penetrating the skin, for example. Here, a coolant, which may be liquid and/or air, may be used to cool a follicular dissection site and/or grafts during penetration. For example, a cooling line may be directed to a graft site to inject a coolant during a dissection and may be stopped after a punch advance motion is stopped. In certain embodiments, a suction or cooling line, or some portion of a follicular dissection device may be connected to a compressor, pump, and/or the like (not shown) that may deliver coolant to cooling line 130, as just an example. Of course, in certain embodiments, a cooling line, such as cooling line 130, may not be used. For instance, heat generated by a follicular extraction procedure may not be excessive because a particular procedure is intermittent, thus allowing natural air cooling between cycles. In addition, body fluids may help as lubricant and cooling medium.

In certain embodiments, a follicular dissection device may include one or more aspiration (e.g., suction) and/or irrigation (e.g., fluid) lines. For instance, in FIG. 2, follicular dissection assembly 102 may include suction line or irrigation line 130. In certain embodiments, suction may be applied to clean a follicular dissection site from body fluids and/or to extract a dissected graft for collection, for example. Likewise, irrigation may be applied to lubricate and/or cool a surface near a dissection site.

In certain embodiments, cooling line or suction line or irrigation line 130 may comprise one or more lines. Thus, in certain embodiments, a single line may perform one or more functions associated with cooling, aspiration and/or irrigation, as a non-limiting example. Similarly, cooling line or suction line or irrigation line 130 may be coupled to follicular dissection assembly 102 in numerous ways. For example, in certain embodiments, a cooling line, suction line or irrigation line, such as line 130, may be located at least partially on an exterior surface of driven assembly 104 and/or a drive assembly 106. Similarly, in certain embodiments, as just an example, one or more of these lines may be coupled externally to driven assembly 104 extending to an end of follicular dissection assembly 102 towards follicular extraction punch 110. Alternatively, one or more of these lines may be located at least partially within driven assembly 104 of follicular dissection assembly 102. Thus, in certain embodiments, one or more of these lines may run from a hollow portion of follicular extraction punch 110 through drive assembly 106. For example, drive 110, drive shaft coupling 112, drive output shaft 114, punch shaft coupling 116, and/or punch holder 118 may be of hollow design. In still another embodiment, a swivel coupling 128 may be applied to a bearing surface of follicular dissection assembly 102. Such a bearing surface may be sealed, such as seals 127 (e.g., O-rings) or other seal elements, and a center part tapped to one or more cooling, suction, and/or irrigation lines, such that those lines may be connected to a cooling, suction, irrigation and/or other device, for example.

In a particular embodiment, driven assembly 104 may have a fluid communication between punch tip 122, punch holder 118, punch holder coupling 116, swivel 128 and tubing 130 used for suction or irrigation. Here, suction line 130 may be coupled to a vacuum pump and canister (not shown) so that the grafts produced by the dissection procedure are collected in to a canister. Punch holder coupling 116 may move relative to connection 130 connected to swivel 128 without imparting a rotating motion on tubing 130. A groove disposed on punch holder coupling 116 may be in fluid communication with suction line 130, such as by means of an opening disposed in swivel 128. Alternatively, the fluid line may be used to clean body fluid from the dissection area or to deliver clean fluid that may be used for lubrication or cooling.

Reference throughout this specification to "one embodiment" or "an embodiment" means that a particular feature, structure, or characteristic described in connection with the embodiment is included in at least one embodiment of claimed subject matter. Thus, the appearance of the phrases "in one embodiment" or "in an embodiment" in various places throughout this specification are not necessarily all referring to the same embodiment. Furthermore, the particular features, structures, or characteristics may be combined in any suitable manner in one or more embodiments.

The term "and/or" as referred to herein may mean "and", it may mean "or", it may mean "exclusive-or", it may mean "one", it may mean "some, but not all", it may mean "neither", and/or it may mean "both", although the scope of claimed subject matter is not limited in this respect.

In the preceding description, various aspects of claimed subject matter have been described. For purposes of explanation, specific numbers, systems and/or configurations were set forth to provide a thorough understanding of claimed subject matter. However, it should be apparent to one skilled in the art having the benefit of this disclosure that claimed subject matter may be practiced without the specific details. In other instances, well-known features were omitted and/or simplified so as not to obscure claimed subject matter. While certain features have been illustrated and/or described herein, many modifications, substitutions, changes and/or equivalents will now occur to those skilled in the art. It is, therefore, to be understood that the appended claims are intended to cover all such modifications and/or changes that fall within the true spirit of claimed subject matter.

What is claimed is:

1. An apparatus, comprising:
    a follicular extraction punch; and
    one or more drivers to affect movement of the follicular extraction punch in a compound motion to be responsive to one or more control signals to be employed to the one or more drivers, wherein the one or more drivers are to be operable to produce at least two advance cutting motions as part of the compound motion, the one or more control signals to be generated at least partially in response to a user selection, via one or more user inputs, of a motion profile from among two or more selectable motion profiles, individual ones of the two or more selectable motion profiles to comprise at least two programmed movement parameters to specify movement of the follicular extraction punch and at least one movement parameter to vary with time for at least a portion of an operation cycle;
    a first of the at least two advance cutting motions to comprise a first axial cutting motion to move the follicular extraction punch to a first distance into a patient's skin and to subsequently retract the follicular extraction punch to a first reference point, and a second of the at least two advance cutting motions to comprise a second axial cutting motion to move the follicular extraction punch to a second distance, to be deeper than the first distance, into the patient's skin and to subsequently retract the follicular extraction punch to a second reference point, the first and second distances to be specified via the user selection.

2. The apparatus of claim 1, the one or more drivers to comprise one or more motors or actuators to produce at least a portion of the compound motion.

3. The apparatus of claim 2, the one or more motors or actuators to comprise at least one of: a direct current (DC) motor; a servo motor; a stepper motor; a solenoid actuator; a voice coil actuator; a pneumatic actuator; a piezoelectric actuator; or a combination thereof.

4. The apparatus of claim 1, further comprising:
    a controller to be communicatively coupled to the one or more drivers;
    the controller to generate the one or more control signals at least partially in response to reception of the user selection of the motion profile.

5. The apparatus of claim 4, the controller to access one or more movement parameters to be associated with the two or more selectable motion profiles and to process at least one of one or more movement parameters based at least partially on the user selection of the motion profile to produce the one or more control signals.

6. The apparatus of claim 5, the one or more control signals to comprise analog signal values or binary digital values to be related to one or more of the speed, angle, or distance values to be associated with the one or more movement parameters.

7. The apparatus of claim 4, the controller to employ the one or more control signals to at least one of the one or more drivers to affect movement of the follicular extraction punch in a compound motion, at least in part.

8. The apparatus of claim 4, the controller to comprise one or more control switches to adjust one or more movement parameters to be associated with the two or more selectable motion profiles.

9. The apparatus of claim 4, the controller to comprise a display to show at least a portion of one or more movement parameters or a number of follicular extractions to be performed.

10. The apparatus of claim 4, the controller to receive one or more feedback signals to be associated with one or more movements of the follicular extraction punch or one or more follicular extractions.

11. The apparatus of claim 4, the controller to comprise an input device to receive the user selection of the motion profile or to receive the user selection of one or more movement parameters.

12. The apparatus of claim 1, further comprising:
a fluid line to transmit fluids via suction or irrigation to be associated with one or more follicular extractions.

13. The apparatus of claim 1, further comprising:
a cooling line to transmit coolant to a follicular dissection site to be associated with one or more follicular extractions.

14. The apparatus of claim 1, further comprising:
an aspiration line to aspirate one or more follicular extractions to be performed by the follicular extraction punch.

15. The apparatus of claim 1, the follicular extraction punch to comprise a component of a driven assembly; the driven assembly and the one or more drivers to be removably attached to one another.

16. The apparatus of claim 1, the one or more drivers to rotate the follicular extraction punch during the at least one advance motion.

17. The apparatus of claim 16, the one or more drivers to rotate the follicular extraction punch during the at least one advance motion at a first rotational speed and to subsequently rotate the follicular extraction punch at a second rotational speed, wherein the first rotational speed is to be different from the second rotational speed.

18. The apparatus of claim 16, the one or more drivers to insert the follicular extraction punch into a patient's skin within a range of about 0 to about 4.0 mm during the at least one advance motion.

19. The apparatus of claim 18, at least a third cutting motion to comprise an oscillation of the follicular extraction punch.

20. The apparatus of claim 1, the one or more drivers to insert the follicular extraction punch into a patient's skin within a range of about 0 to about 4.0 mm during the at least one advance motion.

21. The apparatus of claim 1, the at least one cutting motion to be performed at least partially in response to completion of the at least one advance motion.

22. The apparatus of claim 1, the at least one cutting motion to comprise an oscillation of the follicular extraction punch at a first oscillation speed and subsequently an oscillation of the follicular extraction punch at a second speed of oscillation, the first speed of oscillation to be different from the second speed of oscillation.

23. The apparatus of claim 1, wherein at least one of the programmed movement parameters is to specify a speed of movement of the follicular extraction punch.

24. The apparatus of claim 1, wherein at least one of the programmed movement parameters is to specify an angle of movement of the follicular extraction punch.

25. An apparatus, comprising:
a follicular extraction punch;
one or more drivers to move the follicular extraction punch to perform follicular extraction; and
a controller to be communicatively coupled to the one or more drivers to control at least two advance cutting motions of the follicular extraction punch at least partially in response to a user selection, via one or more user inputs, of one or more time-varying motion profiles from among two or more selectable time-varying motion profiles, individual ones of the two or more selectable motion profiles to comprise at least two programmed movement parameters to specify movement of the follicular extraction punch and at least one movement parameter to vary with time for at least a portion of an operation cycle;
a first of the at least two advance cutting motions to comprise a first axial cutting motion to move the follicular extraction punch to a first distance into a patient's skin and to subsequently retract the follicular extraction punch to a first reference point, and a second of the at least two advance cutting motions to comprise a second axial cutting motion to move the follicular extraction punch to a second distance, to be deeper than the first distance, into the patient's skin and to subsequently retract the follicular extraction punch to a second reference point, the first and second distances to be specified via the user selection.

26. The apparatus of claim 25, a particular time-varying motion profile of the two or more selectable motion profiles to comprise one or more movement parameters, at least one of the one or more movement parameters to vary as a function of time.

27. The apparatus of claim 26, the one or more movement parameters to indicate speed, angle, or distance to be related to one or more cutting motions or one or more advance motions.

28. The apparatus of claim 26, the one or more movement parameters to vary as a function of time to comprise at least one movement to have a variable speed, angle, or distance for at least a portion of an operation cycle.

29. An apparatus, comprising:
a follicular extraction punch; and
one or more drivers to result in movement of the follicular extraction punch in an axial direction, at least in part, the movement of the follicular extraction punch in the axial direction to comprise at least two advance cutting motions of the follicular extraction punch to, at least in part, produce a force to be approximately perpendicular to a scalp at least partially in response to a positioning of the follicular extraction punch approximately perpendicular to the scalp, the movement to be responsive to control signals to be generated at least partially in response to a user selection, via one or more user inputs, of a motion profile from among two or more selectable motion profiles, individual ones of the two or more selectable motion profiles to comprise at least two programmed movement parameters to specify movement of the follicular extraction punch and at least one movement parameter to vary with time for at least a portion of an operation cycle;
a first of the at least two advance cutting motions to comprise a first axial cutting motion to move the follicular extraction punch to a first distance into a patient's skin and to subsequently retract the follicular extraction punch to a first reference point, and a second of the at least two advance cutting motions to comprise a second axial cutting motion to move the follicular extraction punch to a second distance, to be deeper than the first distance, into the patient's skin and to subsequently retract the follicular extraction punch to a second reference point, the first and second distances to be specified via the user selection.

30. An apparatus of claim 29, the movement of the follicular extraction punch in an axial direction to comprise one or more extension or retraction movements to be associated, at least in part, with one or more of the at least two advance cutting motions.

31. The apparatus of claim 30, the one or more of the at least two advance cutting motions to comprise one or more reciprocating motions or one or more vibrating motions.

32. The apparatus of claim 30, the one or more advance motions to comprise one or more extension or retractions motions to be superimposed over one or more axial cutting motions.

33. An apparatus, comprising:
a follicular extraction punch; and
one or more drivers to affect movement of the follicular extraction punch to be responsive to one or more control signals to be employed to the one or more drivers, the one or more drivers to produce at least two advance motions and to rotate the follicular extraction punch during the at least one of the at least two advance motions, the control signals to be generated at least partially in response to a user selection, via one or more user inputs, of a motion profile from among two or more selectable motion profiles, individual ones of the two or more selectable motion profiles to comprise at least two programmed movement parameters to specify movement of the follicular extraction punch and at least one movement parameter to vary with time for at least a portion of an operation cycle;
a first of the at least two advance cutting motions to comprise a first axial cutting motion to move the follicular extraction punch to a first distance into a patient's skin and to subsequently retract the follicular extraction punch to a first reference point, and a second of the at least two advance cutting motions to comprise a second axial cutting motion to move the follicular extraction punch to a second distance, deeper than the first distance, into the patient's skin and to subsequently retract the follicular extraction punch to a second reference point, the first and second distances to be specified via the user selection.

34. The apparatus of claim 33, the one or more drivers to rotate the follicular extraction punch during the at least one advance motion at a first rotational speed and to subsequently rotate the follicular extraction punch at a second rotational speed, the first rotational speed to be different from the second rotational speed.

35. The apparatus of claim 33, the one or more drivers to insert the follicular extraction punch into a patient's skin within a range of about 0 to about 4.0 mm during the at least one advance motion.

36. An apparatus, comprising:
a follicular extraction punch means for extracting one or more hair follicles; and
driver means for affecting movement of the follicular extraction punch means in a compound motion to be responsive to one or more control signals to be employed to the one or more drivers, wherein the one or more drivers are to be operable to produce at least two advance cutting motions as part of the compound motion, the one or more control signals to be generated at least partially in response to a user selection, via one or more user inputs, of a motion profile from among two or more selectable motion profiles, individual ones of the two or more selectable motion profiles to comprise at least two programmed movement parameters to specify movement of the follicular extraction punch means and at least one movement parameter to vary with time for at least a portion of an operation cycle;
a first of the at least two advance cutting motions to comprise a first axial cutting motion to move the follicular extraction punch means to a first distance into a patient's skin and to subsequently retract the follicular extraction punch means to a first reference point, and a second of the at least two advance cutting motions to comprise a second axial cutting motion to move the follicular extraction punch means to a second distance, to be deeper than the first distance, into the patient's skin and to subsequently retract the follicular extraction punch means to a second reference point, the first and second distances to be specified via the user selection.

* * * * *